(12) United States Patent
Carson et al.

(10) Patent No.: US 9,122,783 B2
(45) Date of Patent: Sep. 1, 2015

(54) AUTOMATED LABEL AND VERIFICATION SYSTEMS AND METHODS FOR FILLING CUSTOMER ORDERS OF MEDICAL ITEMS

(71) Applicant: Omnicare, Inc., Cincinnati, OH (US)

(72) Inventors: Bradley E. Carson, Ottawa Hills, OH (US); Jack M. Friday, Monroe, MI (US)

(73) Assignee: Omnicare, Inc., Cincinnati, OH (US)

( * ) Notice: Subject to any disclaimer, the term of this patent is extended or adjusted under 35 U.S.C. 154(b) by 294 days.

(21) Appl. No.: 13/801,070

(22) Filed: Mar. 13, 2013

(65) Prior Publication Data

US 2014/0025545 A1 Jan. 23, 2014

Related U.S. Application Data

(60) Provisional application No. 61/674,649, filed on Jul. 23, 2012, provisional application No. 61/674,644, filed on Jul. 23, 2012.

(51) Int. Cl.
*G06F 17/00* (2006.01)
*G06F 19/00* (2011.01)
*G06Q 30/00* (2012.01)
*G07F 17/00* (2006.01)

(52) U.S. Cl.
CPC ........ *G06F 19/3462* (2013.01); *G06F 19/3456* (2013.01); *G06Q 30/018* (2013.01); *G07F 17/0092* (2013.01)

(58) Field of Classification Search
CPC ..... G07F 17/0092; G07F 11/48; G07F 11/54; G06Q 10/087; G06F 19/3462
USPC .......................................... 700/242; 221/122
See application file for complete search history.

(56) References Cited

U.S. PATENT DOCUMENTS

| | | | |
|---|---|---|---|
| 3,606,014 A | 9/1971 | Linn | |
| 3,656,616 A | 4/1972 | Wallington | |
| 3,882,316 A | 5/1975 | Garris | |
| 4,011,155 A | 3/1977 | Feurstein et al. | |

(Continued)

FOREIGN PATENT DOCUMENTS

| | | |
|---|---|---|
| CA | 2509120 A1 | 2/2006 |
| EP | 1388336 A1 | 11/2004 |
| EP | 1889802 A2 | 2/2008 |

OTHER PUBLICATIONS

U.S. Patent and Trademark Office, Non-final Office Action in related U.S. Appl. No. 13/801,017, dated Oct. 22, 2014 (19 pages).

*Primary Examiner* — Timothy Waggoner

(74) *Attorney, Agent, or Firm* — Wood, Herron & Evans, LLP

(57) ABSTRACT

Systems and methods for filling a customer order. An automated label and verification machine is used to print and apply patient labels to products containing medical items and then verify the product label and patient label on each of the products. In order to supply the automated label and verification machine with a batch of different products making up the customer order, a user is sent to a storage carousel and prompted to pick the products from storage locations rotated into location adjacent to a door in the cage surrounding the storage carousel. The use of the storage carousels maximizes the number of distinct products and amount of those products that may be stored in close relation to the automated label and verification machine, thereby making the process more space and time efficient.

19 Claims, 25 Drawing Sheets

(56) References Cited

U.S. PATENT DOCUMENTS

| | | | | |
|---|---|---|---|---|
| 4,053,056 | A | 10/1977 | Day | |
| 4,530,199 | A | 7/1985 | Manservisi et al. | |
| 5,101,609 | A | 4/1992 | Cook | |
| 5,406,770 | A | 4/1995 | Fikacek | |
| 5,568,715 | A | 10/1996 | Ebel et al. | |
| 5,593,267 | A | 1/1997 | McDonald et al. | |
| 5,597,995 | A * | 1/1997 | Williams et al. | 235/375 |
| 5,660,305 | A | 8/1997 | Lasher et al. | |
| 5,720,154 | A | 2/1998 | Lasher et al. | |
| 5,771,657 | A | 6/1998 | Lasher et al. | |
| 5,880,443 | A | 3/1999 | McDonald et al. | |
| 5,883,370 | A | 3/1999 | Walker et al. | |
| 5,905,653 | A * | 5/1999 | Higham et al. | 700/244 |
| 5,963,453 | A | 10/1999 | East | |
| 6,158,193 | A | 12/2000 | Focke et al. | |
| 6,317,648 | B1 | 11/2001 | Sleep et al. | |
| 6,373,520 | B1 | 4/2002 | Cadieux, Jr. et al. | |
| RE37,829 | E | 9/2002 | Charhut et al. | |
| 6,449,927 | B2 | 9/2002 | Hebron et al. | |
| 6,464,142 | B1 * | 10/2002 | Denenberg et al. | 235/462.46 |
| 6,471,089 | B2 | 10/2002 | Liff et al. | |
| 6,522,945 | B2 | 2/2003 | Sleep et al. | |
| 6,575,216 | B2 | 6/2003 | Yang | |
| 6,655,015 | B2 | 12/2003 | Kraenzle | |
| 6,735,497 | B2 | 5/2004 | Wallace et al. | |
| 6,748,295 | B2 * | 6/2004 | Tilles et al. | 700/241 |
| 6,776,304 | B2 | 8/2004 | Bossi et al. | |
| 6,814,254 | B2 | 11/2004 | Liff et al. | |
| 6,814,255 | B2 | 11/2004 | Liff et al. | |
| 6,847,861 | B2 * | 1/2005 | Wangu et al. | 700/242 |
| 6,892,512 | B2 | 5/2005 | Rice et al. | |
| 6,970,769 | B2 | 11/2005 | Rice et al. | |
| 6,971,213 | B2 | 12/2005 | Battisti | |
| 6,983,579 | B2 | 1/2006 | Rice et al. | |
| 7,006,893 | B2 | 2/2006 | Hart et al. | |
| 7,010,899 | B2 | 3/2006 | McErlean et al. | |
| 7,047,706 | B2 | 5/2006 | Kraenzle | |
| 7,084,738 | B2 * | 8/2006 | Bastian, II | 340/5.92 |
| 7,086,558 | B1 * | 8/2006 | Pixley et al. | 221/9 |
| 7,100,792 | B2 | 9/2006 | Hunter et al. | |
| 7,185,477 | B2 | 3/2007 | Rice et al. | |
| 7,269,476 | B2 | 9/2007 | Ratnakar | |
| 7,334,379 | B1 | 2/2008 | Siegel et al. | |
| 7,386,965 | B2 | 6/2008 | McErlean et al. | |
| RE40,453 | E | 8/2008 | Lasher et al. | |
| 7,409,977 | B2 | 8/2008 | Rice et al. | |
| 7,412,814 | B2 | 8/2008 | Rice et al. | |
| RE40,510 | E | 9/2008 | Lasher et al. | |
| 7,427,002 | B2 | 9/2008 | Liff et al. | |
| 7,430,838 | B2 | 10/2008 | Rice et al. | |
| 7,440,817 | B2 | 10/2008 | Fu | |
| 7,467,093 | B1 | 12/2008 | Newton et al. | |
| 7,513,091 | B2 | 4/2009 | Moodley | |
| 7,676,299 | B2 * | 3/2010 | Clarke et al. | 700/231 |
| 7,721,512 | B2 | 5/2010 | Siegel et al. | |
| 7,753,085 | B2 | 7/2010 | Tribble et al. | |
| 7,774,097 | B2 | 8/2010 | Rosenblum | |
| 7,882,680 | B2 | 2/2011 | Siegel et al. | |
| 7,984,602 | B2 | 7/2011 | Kraenzle | |
| 8,002,174 | B2 | 8/2011 | Coyne, III et al. | |
| 8,121,725 | B2 * | 2/2012 | Baker et al. | 700/236 |
| 8,215,540 | B2 | 7/2012 | Szesko et al. | |
| 8,231,749 | B2 | 7/2012 | Dent et al. | |
| 8,262,842 | B2 | 9/2012 | Szesko et al. | |
| 8,744,621 | B2 * | 6/2014 | Michael | 700/242 |
| 2002/0026768 | A1 | 3/2002 | Duncan et al. | |
| 2002/0117405 | A1 | 8/2002 | Wang et al. | |
| 2003/0088333 | A1 | 5/2003 | Liff et al. | |
| 2003/0125837 | A1 | 7/2003 | Walace et al. | |
| 2003/0176942 | A1 | 9/2003 | Sleep et al. | |
| 2004/0210341 | A1 | 10/2004 | Wallace et al. | |
| 2004/0215486 | A1 | 10/2004 | Braverman | |
| 2006/0161294 | A1 | 7/2006 | DiMaggio | |
| 2006/0161298 | A1 | 7/2006 | DiMaggio | |
| 2006/0277269 | A1 | 12/2006 | Dent et al. | |
| 2007/0102109 | A1 | 5/2007 | Katritzky et al. | |
| 2007/0271001 | A1 | 11/2007 | Ratnakar | |
| 2008/0172305 | A1 | 7/2008 | Estes et al. | |
| 2008/0229718 | A1 | 9/2008 | Feehan et al. | |
| 2009/0173779 | A1 * | 7/2009 | Szesko et al. | 235/375 |
| 2011/0202481 | A1 | 8/2011 | Lang et al. | |

* cited by examiner

AUTOMATED LABEL AND VERIFICATION SYSTEMS AND METHODS FOR FILLING CUSTOMER ORDERS OF MEDICAL ITEMS

CROSS-REFERENCE TO RELATED APPLICATIONS

This application claims the benefit of U.S. Patent Application No. 61/674,649, filed Jul. 23, 2012, and also claims the benefit of U.S. Patent Application No. 61/674,644, filed Jul. 23, 2012, the disclosures of which are incorporated by reference herein in their entirety.

BACKGROUND

Conventionally, pharmacies have filled large quantities of customer orders for skilled nursing facilities, assisted living facilities, independent living facilities, group homes, hospice facilities and other configurations of the nursing home industry and institutionalized long term care industry with a labor-intensive, pharmacist-based, assembly line method. Typically, a customer order is comprised of patient prescriptions issued by a physician and fulfilled under close pharmacist supervision. In general, filling of prescriptions consists of executing the customer order by associating the correct pharmaceutical product or medical item with the correct prescription label. Generally, such filling is performed by pharmacists, technicians, or combinations of these individuals. The prescription labels with patient information (hereafter referred to as "patient labels") are typically printed out in batch form with flag labels for every patient label regardless of whether the product requires a flag label or not, and these batches of labels are carried around by the individuals collecting the packages from bulk inventory. Products in the form of a variety of packages (e.g., 24-Hour, 7-day, 14-day, 15-day, 30-day dosages, and individually by form and strength), are removed from bulk inventory and, thereafter, a prescription label is printed and manually applied to the appropriate product.

Following collection of the products and application of the patient labels, the application may then be verified in one of many ways. It can be checked against a master order sheet (MAR) or visually checked by the technician, pharmacist, or a combination of these individuals. The correct patient label application can also be verified by manually scanning the barcode or indicia on the prescription label and looking up the required prescription medication name, strength and dose which is then matched to the barcode or indicia that is scanned on the product/package label. If these attributes match, then the patient centric labeled product/package is considered to be verified. Once each patient centric labeled product is verified, then the patient centric labeled products are grouped and presorted into containers. The grouping and presorting of products can be done based on the patient, the residence of the patient or shipping location, the delivery method or carrier, time of day, or any other styled grouping of such. The pre-sorted containers are broken down in a sorting area where the products are individually scanned and placed into the shipping containers (e.g., boxes, bags, bins, or totes). Typically at this point, the label application is re-verified and the product's association with the particular shipping container is checked. This is a barcode-scanning step where the package label, the prescription label, and the shipping container (or any combination of these items) are confirmed to be correct. By the time a labeled and verified product is correctly placed in a shipping tote, it has typically been handled or touched by an individual up to approximately 11-13 times. The large number of touches required to process products represents inefficiencies and increases the potential for human error.

In an attempt to address these process inefficiencies and reduce the number of required human touches for each product, an automated label and verification (ALV) system has been developed as described in U.S. Pat. No. 8,215,540 to Szesko et al., which is co-owned by the assignee of the present invention, and is hereby incorporated by reference herein in its entirety. The automated label and verification system includes a turntable configured to receive a stack of blister cards or a series of product boxes. Robotic machinery scans the product labels on these blister cards and product boxes, positions the cards/boxes on the turntable, rotates the cards/boxes to a label printing and application station where a patient label is printed and applied on demand, scans both labels for verification of proper labeling, and rotates the cards/boxes to a removal station where a robot moves the cards/boxes into totes for downstream processing and shipping. The automated label and verification system has greatly increased the efficiency and improved the quality of the prescription filling process for blister cards and product boxes by automating the label printing, application, and verification process to reduce human touches required.

The ALV system described above must be supplied with the blister cards and product boxes by an operator. As shown in FIG. 1, the operator 10 has conventionally retrieved batches of blister cards and product boxes for a particular customer order from a pick-to-light system 12 located adjacent to the turntable (not shown in FIG. 1). The pick-to-light system 12 includes a plurality of pick-to-light inventory racks 14 arranged in aisles, each inventory rack 14 including a plurality of shelves 16 with separated storage locations 18 holding bulk shipper cases 20 containing the medical items. As well understood, the operator 10 must walk along each of the aisles of pick-to-light inventory racks 14 to identify all illuminated storage locations 18 containing medical items that must be picked for a current customer order. As the pick-to-light system 12 illustrated includes about 312 storage locations 18 in nearly 1000 square feet of flow space, this process of walking to each of the inventory racks 14 and collecting the picks can be a time-consuming process for each customer order. Furthermore, pharmacies handle many more than 312 distinct medical items and pharmaceuticals in these blister cards and product boxes, so the pick-to-light system 12 is only capable of holding and dispensing a portion of the medical items needed for customer orders (preferably the most often filled medical items). All other medical items must be retrieved from non-pick-to-light (NPTL) storage locations using the conventional process of carrying a pick ticket through these NPTL storage locations and then staging and pre-sorting batches of medical items into a plurality of totes to be used at the ALV system.

Therefore, there remains room for improvement in the methodologies used by pharmacies to fill prescriptions against customer orders. More specifically, it would be desirable to minimize the human movements required to fill a customer order while increasing efficiency for the picking, labeling, and verification process.

SUMMARY OF THE INVENTION

According to one embodiment, a method for filling a customer order containing at least one product to be labeled and verified includes receiving a batch of products to be picked from a storage carousel surrounded by a cage having a door. Each product includes a medical item. Pick instructions are generated for each of the batch of products to be picked, the pick instructions including an indication of a storage location in the storage carousel. The method also includes rotating the storage carousel to move a first storage location holding a first product of the batch of products adjacent to the door of the cage to provide access for the user to remove the first product from the first storage location. The user is prompted to remove the first product by illuminating an associated pick module on the cage adjacent to the first storage location, and an input is received from the user to confirm that the first product has been removed. The rotating, prompting, and receiving input steps are repeated for each of the products in the batch of products until all products are removed from the storage carousel. The products are then labeled with a patient label, and it is verified that a correct patient label was applied to each of the products in the customer order.

In one aspect, each of the products also includes a product label. The labeling and verification process may be performed by prompting the user to insert the batch of products into product inlets associated with an automated label and verification machine. The automated label and verification machine labels each of the batch of products with a patient label, and then verifies that the product label and the patient label are correctly applied to each of the products that were inserted into the product inlets. The labeling and verifying steps may also include automatically verifying the product label on each of the products and transferring each of the products with a verified product label onto a conveyor defining a workflow path for processing the products. Along the workflow path, a patient label is printed for each of the products and applied to the products, and then the product label is verified to make sure it matches the patient label on each of the products moving along the workflow path.

The system may include a plurality of storage carousels in some embodiments. The batch of products received for a customer order may include products located in the plurality of storage carousel, and the user may then be prompted to move to a different storage carousel after each of the products contained in a first storage carousel have been removed from the first storage carousel. The products may also be contained in pick-to-light racks as well as the storage carousels. The storage locations on the pick-to-light racks are illuminated to prompt the user to remove the products location in the corresponding storage locations. Regardless of whether the system includes one or more storage carousels and pick-to-light racks, the user may provide input to confirm removal of an item from a storage location by depressing a press button on the pick modules located on the cages of the storage carousels. In another alternative, the user may provide input to confirm removal of an item from a storage location by scanning the product with a hand scanner that the user carries around to each of the storage locations. The hand scanner may also provide a human machine interface (HMI) for providing prompts to the user when needed. The user may be prompted to remove multiple items stored in a single storage location when multiples of the same item are needed for the batch of products, and the system will prompt the operator to continue removing items until the desired number has been removed.

In another aspect, the storage carousel includes a light curtain optical sensor adjacent the door which detects an entry of a user's arm into the storage carousel so that rotating movement of the storage carousel is stopped anytime a user's arm is inside the cage and at risk of injury. The storage carousel may be used to deliver controlled substances to authorized users filling customer orders. In this regard, the door on the cage is motorized and at least some of the storage bins in the storage carousel contain controlled substances. The motorized door is closed to prevent access to the storage bins before any pick information has been provided to the user. The method includes verifying identification data provided by the user to determine if the user is authorized to remove controlled substances. If the user is authorized, the motorized door only opens when the first location has been rotated to the door of the cage. This operation prevents even the authorized user from gaining temporary access to storage bins in the storage carousel that should not be accessed for the customer order. Moreover, controlled substances of different schedule levels may be kept in different vertical columns of storage bins formed by the storage carousel, thereby separating controlled substances of different schedule levels in independent pie-piece-shaped portions of the storage carousel. As one vertical column is all that is ever accessible at the door, the method includes rotating the storage carousel such that the portions of the storage carousel containing controlled substances of a schedule level higher than what the user is authorized to remove are never rotated past the door, thereby preventing a user from having even temporary access to controlled substances of a schedule level higher than what the user is authorized to remove.

When the pick instructions are generated for the products to be picked from the storage carousel, a sequence of products may be determined by calculating the most efficient manner of presenting the products to the door of the cage. This process includes including identifying any groups of products in one or more storage locations that may be presented to the door of the cage simultaneously, and also sequencing the product removals to limit the amount of rotation that the storage carousel must undergo between each product removal. Therefore, the movements of the storage carousel are minimized by following the sequence of products that is determined. In another alternative, the pick instructions may be generated by selecting which of multiple storage locations containing a particular product to be removed should be used for the current customer order. The selection can be made based on various types of logic, including but not limited to: "First In First Out" logic that removes products in the order placed into the storage carousel, and "First Expired First Out" logic to remove products that will expire soonest from the storage carousel. Consequently, the generation of pick instructions can be used to optimize both the efficiency of the labeling and verification process and the inventory management of the storage carousel.

During system downtimes or between filling of customer orders, the storage carousels will require restocking Thus, the method also includes a restocking process including prompting a user to input data identifying a product to be restocked and a quantity of the product available to place into the storage carousel. At least one storage location is determined that is free to receive the product, and the storage carousel is rotated to present the at least one storage location to the door of the cage. The pick modules are selectively operated to prompt the user to place the product to be restocked into the at least one storage location. The user then provides an indication that the product has been restocked into the at least one storage location, and the process is repeated for each other product to be restocked.

In another embodiment according to the invention, a system is configured to fill a customer order containing at least one product to be labeled and verified. The system includes a storage carousel having a plurality of storage bins on a plurality of shelves. The storage bins receive bulk inventory of a product. A cage surrounds the storage carousel and includes a door configured to provide selective access to one of the storage bins on each shelf of the storage carousel. A plurality of pick modules is mounted on the cage and is associated with each of the shelves. A controller having a processor and a memory is configured to execute program code resident in the memory. The program code is operable to identify a customer order and receive a batch of products to be picked from the storage carousel, the batch of products including medical items contained in the customer order, actuate rotation of the storage carousel to provide access to one of the products in the batch, prompt the user to remove the product from the storage carousel by illuminating the pick modules, and continue rotation and illumination steps until all products for the batch have been removed from the storage carousel. The system also includes an automated label and verification machine configured to receive the batch of products, label the products with patient labels, and verify that the patient labels match product labels located on the products.

The automated label and verification machine may also include a conveyor defining a workflow path for processing the products. A label application station is arranged about the workflow path and is configured to print and apply a patient label onto each of the products. A vision inspection station is arranged about the workflow path and is configured to independently verify that the product label on each of the products matches a patient label after application of the patient label to the product. An unloading station is also included to transfer labeled and verified products away from the conveyor. The system may also include a light curtain optical sensor coupled to the controller and located adjacent to the door. The optical sensor detects when a user's arm enters into the cage so that rotation of the storage carousel can be stopped to prevent injury to the user. A pharmacy host server may also be provided to generate the batches of products for a customer order and send the batches of products to the controller for use during filling of the customer orders.

In another aspect, the system includes a plurality of storage carousels each including a plurality of storage bins on a plurality of shelves, a cage, a door, and pick modules. The system also includes a human machine interface that is configured to provide instructions to the user to indicate which of the plurality of storage carousels to move to in order to pick a product for the customer order. The human machine interface may include an alphanumeric display mounted on the cage of each of the storage carousels adjacent to the pick modules. Alternatively, the human machine interface may be provided by a display screen on a hand scanner carried by the user between the plurality of storage carousels. Therefore, the user may always be notified where the next product in a batch of products may be obtained, thereby increasing the efficiency of the process. The system enables more products to be stored in smaller area close in proximity to the automated label and verification machine.

Various additional features and advantages of the invention will become more apparent to those of ordinary skill in the art upon review of the following detailed description of the illustrative embodiments taken in conjunction with the accompanying drawings.

DETAILED DESCRIPTION

Embodiments consistent with aspects of the current invention provide for a system, apparatus and method for filling a customer order with a plurality of products, where each product includes at least one medical item or medication. More specifically, an operator may use an automated label and verification (ALV) system to label medical items having product labels with patient labels containing information regarding the end consumer or patient. Unlike conventional manual based systems, each medical item in an ALV system is moved robotically or by machinery through a plurality of stations that scan the product label, generate and apply an appropriate patient label for that medical item, and verify that the correct patient label and product label are matched before sending the medical item to downstream processing. The automation of the labeling and verification process eliminates multiple human touches needed during the conventional manual process. In addition, the ALV system labels and verifies significantly more medical items per minute than the conventional manual process.

Figure 1:
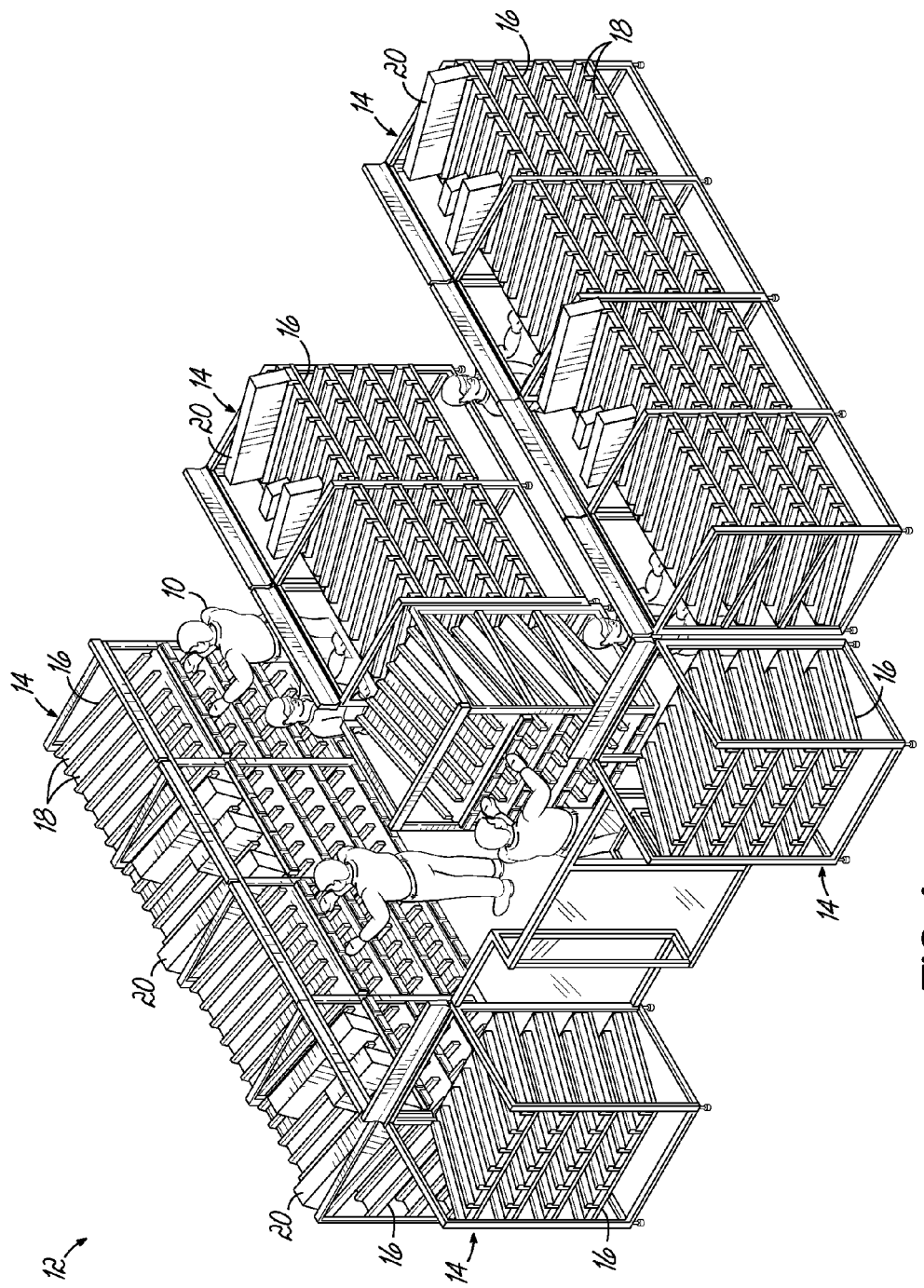
FIG. 1 is a perspective view of a conventional pick-to-light system used with an automated label and verification (ALV) system.

Batches of medical items must be delivered to the machinery of ALV system for the machinery to operate the automated process. In some embodiments consistent with the invention, these batches of items are advantageously stored in a plurality of ALV carousel units that are used to bring bulk inventory to a single picking location for retrieval by the operator. Unlike the conventional provision of plurality of pick-to-light racks 12 arranged in multiple aisles as shown in FIG. 1, the ALV carousel units store a higher number of products within a significantly reduced floor space. The ALV carousel units still enable operators to use a pick-to-light interface to obtain batches of medical items to put into the machinery of the ALV system. Accordingly, the operator only needs to take a few steps between the multiple ALV carousel units to put together an entire batch of picked medical items that will be labeled and verified at the machinery of the ALV system. When used in combination with the remainder of the ALV system, the ALV carousel units further enhance the efficiency and accuracy of the filling process for customer orders including medical items and products.

Figure 2:
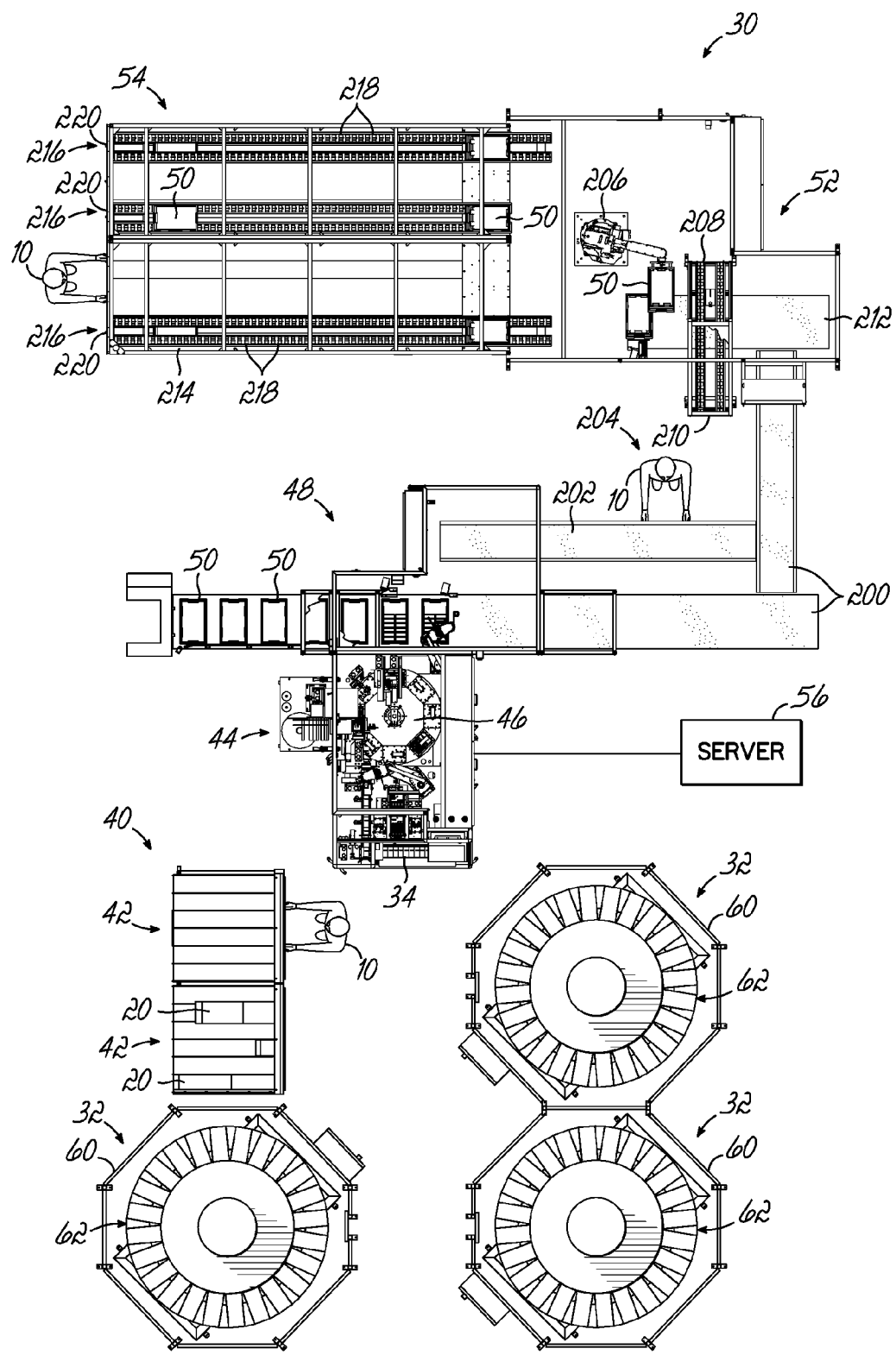
FIG. 2 is a top schematic view of an ALV system according to one embodiment of the current invention, the ALV system including a plurality of ALV carousel units.

FIG. 2 illustrates one embodiment of an Automated Label Verify (ALV) system 30. The ALV system 30 is an automated pharmacy order dispensing system that enables pharmacy orders to be processed in an efficient manner using logic-based methodologies. To facilitate discussion of the ALV system 30 and these methodologies, a general overview of the ALV system 30 is provided below, followed by a detailed review of components and operation of the ALV carousel units 32 used with the ALV system 30. The ALV carousel units 32 expand the bulk inventory that may be stored in close proximity to product inlets 34 that lead to the machinery of the ALV system 30. The ALV carousel units 32 also reduce the number of pre-sorting and post-sorting steps that must be undertaken by human operators 10 when processing customer orders at the pharmacy.

By way of background, the ALV system 30 may be used to dispense and fulfill prescriptions in products defining at least two different form factors. The products are shown in the form of blister cards 36 (described below with reference to FIG. 10) that hold a number of pills, liquids, ointments, gels, creams, injectables, etc., and product boxes 38 (described below with reference to FIG. 11) that may be prepackaged with individual thermoformed blister strips (not shown) or other packages of pharmaceuticals or other medical items. The product boxes 38 may also be loaded with non-pharmaceutical types of medical items that may be needed by the end consumer. Although the ALV system 30 of the exemplary embodiment is designed for these two form factors 36, 38, it will be appreciated that aspects of the invention described below—especially the methodologies discussed in connection with the operation of the ALV system 30—are not necessarily limited to such form factors 36, 38. Other types of packagings could be accommodated should such accommodation be important for a particular pharmacy's needs.

With this general understanding of the products processed by the ALV system 30, an overview of an exemplary embodiment of the ALV system 30 will now be explained with reference to FIG. 2. The ALV system 30 includes a pick-to-light system 40 including a plurality of ALV carousel units 32 and optionally also pick-to-light racks 42 that hold bulk shipper cases 20 containing the products 36, 38 (e.g., the blister cards and product boxes). The ALV system 30 also includes an ALV machine 44 that processes the products along a turntable 46 (also referred to as a dial conveyor), a tote conveyor system 48 that supplies containers 50 for receiving the products 36, 38 processed by the ALV machine 44, and a tote handling system 52 that moves filled containers 50 from the tote conveyor system 48 onto a tote rack 54 leading to locations for downstream processing. The ALV machine 44 processes products 36, 38 pulled by an operator 10 from the ALV carousel units 32 and from the optional racks 42 of the pick-to-light system 40 by passing them through various stations designed to serve one or more specific functions. The tote conveyor system 48 and the tote handling system 52 controllably move totes 50 of labeled and verified products 36, 38 from the ALV machine 44 to a location convenient for downstream processing. The ALV system 30 also includes an ALV Order Manager (AOM) control system interfacing with a pharmacy host server 56 (shown schematically in FIG. 2) to manage information sent to and from the ALV machine 44 and pick-to-light system 40.

As shown generally in the top plan view of FIG. 2, the ALV system 30 includes a plurality of ALV carousel units 32 each including a cage 60 surrounding a moveable storage carousel 62. Now turning to FIGS. 3 through 6, one of the ALV carousel units 32 according to the exemplary embodiment of the invention is described in detail. In addition to the cage 60 and storage carousel 62, the ALV carousel unit 32 includes a controller box 64 configured to contain the controllers that drive elements of the storage carousel 62 and interactions with the operator 10 as described in detail below. To this end, the ALV carousel unit 32 includes a human machine interface (HMI) 66 having a light tree 68 with a plurality of pick modules 70 mounted on the cage 60. The human machine interface 66 may include additional elements such as order control modules in other embodiments. The pick modules 70 are operatively coupled to the controller box 64 such that the pick modules 70 interact with the levels of the storage carousel 62 and instruct the operator 10 where to retrieve medical items or products from in the storage carousel 62. The cage 60 selectively provides access to only a small portion of the storage carousel 62. The storage carousel 62 includes a plurality of storage locations 72 that may be rotated into position for access by the operator 10 and are described in further detail with reference to FIGS. 4 through 5B below. As a result, the storage carousel 62 effectively moves a plurality of medical items and products to the operator 10 for retrieval and then scanning and labeling at the ALV machine 44, rather than requiring an operator 10 to walk up and down aisles of storage racks of bulk inventory to collect batches of medical items and products for the ALV machine 44.

The inventory stored in all of the storage carousels 62 is monitored and managed by communication between the controller boxes 64 on the ALV carousel units 32 and the pharmacy host server 56. The server 56 may also communicate with a central control station (not shown) that allows a pharmacist to log in to activate and monitor the labeling and verification process carried out at the ALV system 30. It will be understood that while three ALV carousel units 32 are shown in the ALV system 30 of the exemplary embodiment, more or fewer ALV carousel units 32 may be used depending on the volume and number of medical items and products needed for a typical day of prescription filling at the pharmacy. Additionally, the layout of ALV carousel units 32 is shown with doors 74 in the cages 60 facing generally towards one another to minimize the steps needed to move between the ALV carousel units 32, but this layout may be modified in other embodiments consistent with the invention.

Figure 2A:
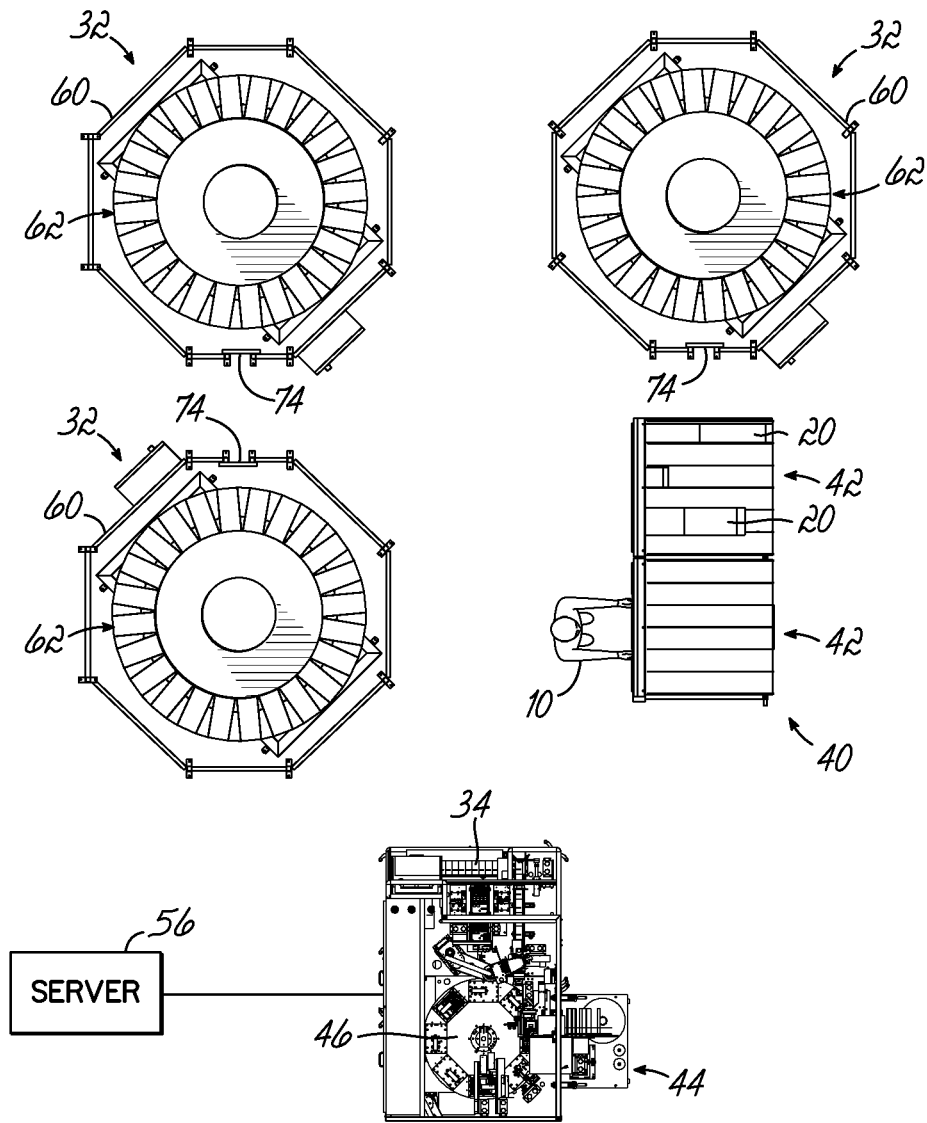
FIG. 2A is a top schematic view of an ALV system according to another embodiment, with a slightly modified layout of ALV carousel units from the layout shown in FIG. 2.

Following up on this latter point, one alternative embodiment of the layout of the ALV carousel units 32 is shown in FIG. 2A. To this end, the adjacent ALV carousel units 32 have been separated in this alternative layout such that the doors 74 in the corresponding cages 60 can be located on either side of the small walking space between the cages 60. Consequently, an operator can stand between the two doors 74 and have ready access to both ALV carousel units 32 without taking a step or moving away from either of the ALV carousel units 32. This layout is just one of many possible orientations of the cages 60 and doors 74 of the ALV carousel units 32 though, and any reconfiguration of the layout may be included within the scope of this invention as needed to suit the requirements of the end user.

Figure 3:
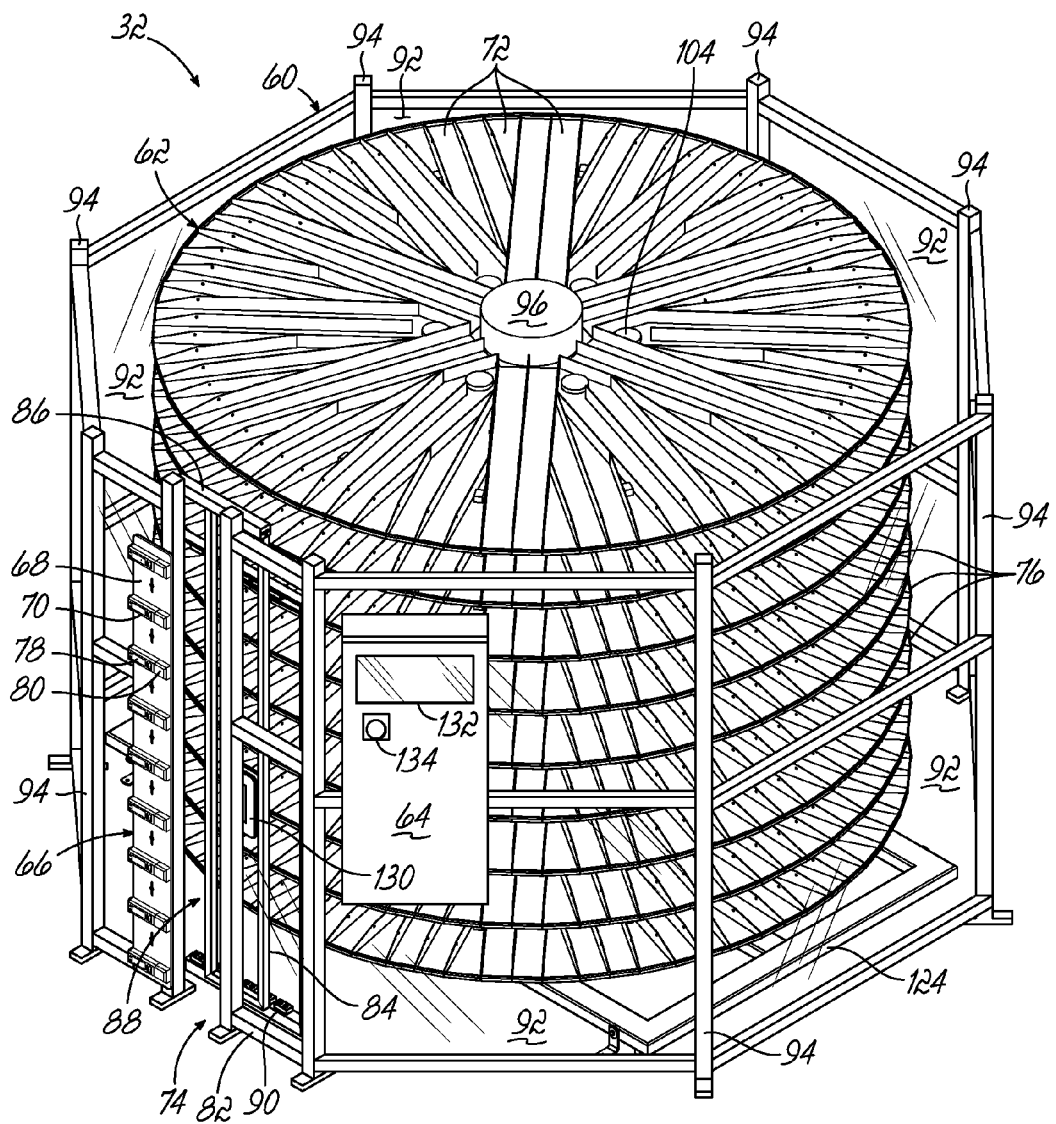
FIG. 3 is a perspective view of one of the ALV carousel units of FIG. 2, the ALV carousel unit including a storage carousel and a cage surrounding the storage carousel.

With continued reference to FIG. 3, the pick modules 70 are positioned generally at the height of each shelf 76 on the storage carousel 62 and include a four-character alphanumeric display 78 configured to show a number of items to be picked from the particular storage location 72 at the corresponding shelf 76. The pick modules 70 are mounted directly on the cage 60 adjacent to the door 74 such that the pick modules 70 may be readily associated with the adjacent shelf 76 of the storage carousel 62. Furthermore, the pick modules 70 include at least one button 80 configured to receive input from the operator 10 indicating that items have been removed from the storage location 72. The pick modules 70 are connected to a bay controller (not shown) located in the controller box 64 and configured to communicate with the pharmacy host server 56. In embodiments in which the ALV carousel unit 32 includes an order control module, that order control module may include a twelve-character alphanumeric display configured to display the status of an order or batch being picked at the pick-to-light system 40. However, when only one batch is being picked at a time at the pick-to-light system 40, the pick modules 70 are sufficient without any additional elements to instruct an operator 10 where to retrieve all medical items needed for the batch to be labeled and verified at the ALV machine 44. In the event that multiple items from the same storage location need to be removed for the batch of items, then the pick modules 70 will continue illuminating until the operator indicates that the desired number of items has been removed.

The cage 60 includes the door 74, which is located adjacent to and extending from the light tree 68. The door 74 includes a stationary door panel 82 connected to the remainder of the cage 60 and a moveable door panel 84 slideably mounted on rails 86 on the stationary door panel 82. The door 74 may be manually moved or motorized in various embodiments of the invention. When the moveable door panel 84 moves to an open position behind the stationary door panel 82, a tall elongate opening 88 is formed in the cage 60 providing access to the storage carousel 62 from outside the cage 60. Adjacent to this opening 88 is provided a light curtain optical sensor 90 that operates to detect any entries of an operator's arm into the ALV carousel unit 32 from outside the cage 60. These elements of the door 74 are also shown in further detail with reference to FIG. 6 below. The remainder of the cage 60 is defined by a plurality of cage panels 92 connected in series to form a roughly octagonal shaped enclosure to surround the storage carousel 62. The cage panels 92 define corner joints 94 that may be connected to adjacent cage panels 92 and secured to the floor to prevent unintentional removal of the cage 60 from the storage carousel 62. It will be understood that these cage panels 92 may be welded together at the corner joints 94 in some embodiments of the invention. In FIG. 3 and other figures, the cage panels 92 are shown with a clear Plexiglas-type appearance for illustrative purposes, but the exemplary embodiment of the cage panels 92 includes metal wire mesh caging that blocks unintended entry into the ALV carousel unit 32 but enables some visibility of the storage carousel 62 within the cage 60. However, alternative types of blocking cage panels 92 such as Plexiglas, aluminum, or light grade steel panels may be used in other embodiments of the ALV carousel unit 32.

Figure 4:
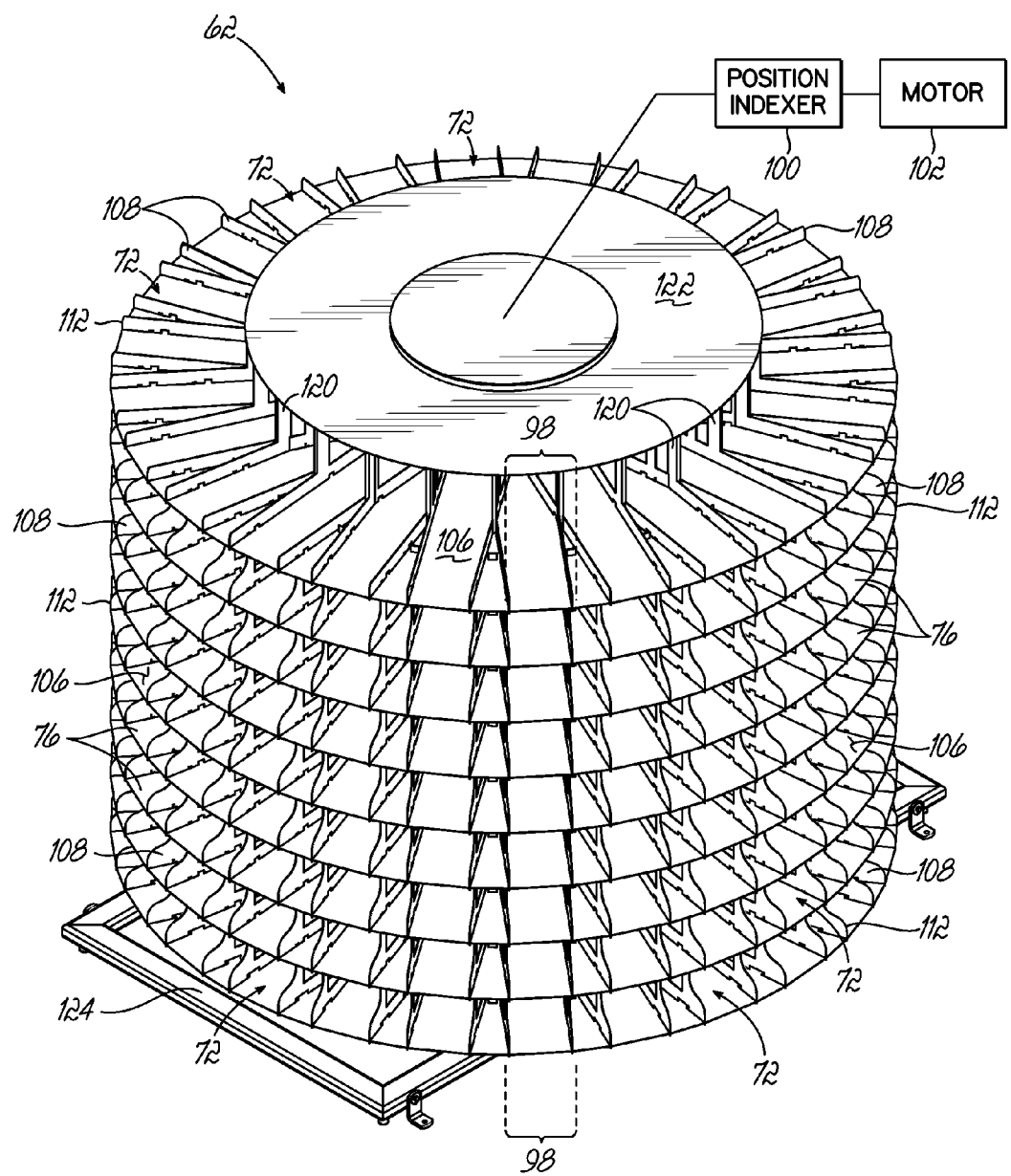
FIG. 4 is a perspective view of the storage carousel used with the ALV carousel unit of FIG. 3.

As described briefly above, the storage carousel 62 includes a plurality of shelves 76 defining a plurality of radially-oriented storage bins 72 (also referred to as storage locations) extending outwardly from a central shaft 96. The storage bins 72 are sized with a width corresponding closely to the size of standard medical item product boxes 38 or bulk shipper cases 20 of blister cards 36, each of which generally require a width of about 7 inches across. However, the overall arrangement of the bins 72 and the size of the bins 72 and the distance between the shelves 76 may be increased or decreased to increase or decrease the total amount of storage locations. The opening 88 through the door 74 is also sized slightly larger than the size of these storage bins 72 such that access is only provided to the storage bin 72 directly facing the opening 88 when the operator 10 reaches into the ALV carousel unit 32. As a result, the storage carousel 62 must be indexed during rotation to ensure that the intended column of storage bins 98 (see FIG. 4 for an example) on the shelves 76 are appropriately aligned with the opening 88. With reference to FIG. 4, the storage carousel 62 includes a position indexer 100 and a motor 102 operatively coupled to the central shaft 96 to drive indexed rotation of the storage carousel 62. As shown most clearly in FIG. 5A, the storage carousel 62 also includes a plurality of alignment shafts 104 that extend through the shelves 76 and are also driven by the motor 102. The central shaft 96 and the alignment shafts 104 provide reliable support and rotation driving power to each of the nine shelves 76 shown in the exemplary embodiment even when all of the storage bins 72 are loaded with product boxes 38 and blister cards 36. In the exemplary embodiment, the motor 102 is operable to rotate the storage carousel 62 with a controlled movement of 180 degrees in less than about 2.5 seconds. This rapid rotation enables the storage carousel 62 to quickly be located at the next location after an operator 10 retrieves all medical items from the column of storage locations 98 and extinguishes all of the pick modules 70 illuminated for that column of storage locations 98. However, the rotation is not so rapid as to cause the medical items on the storage carousel 62 to be forced off the shelves 76 by centrifugal force (e.g., the rotation is controlled via acceleration and deceleration curves and control algorithms).

Figure 5A:
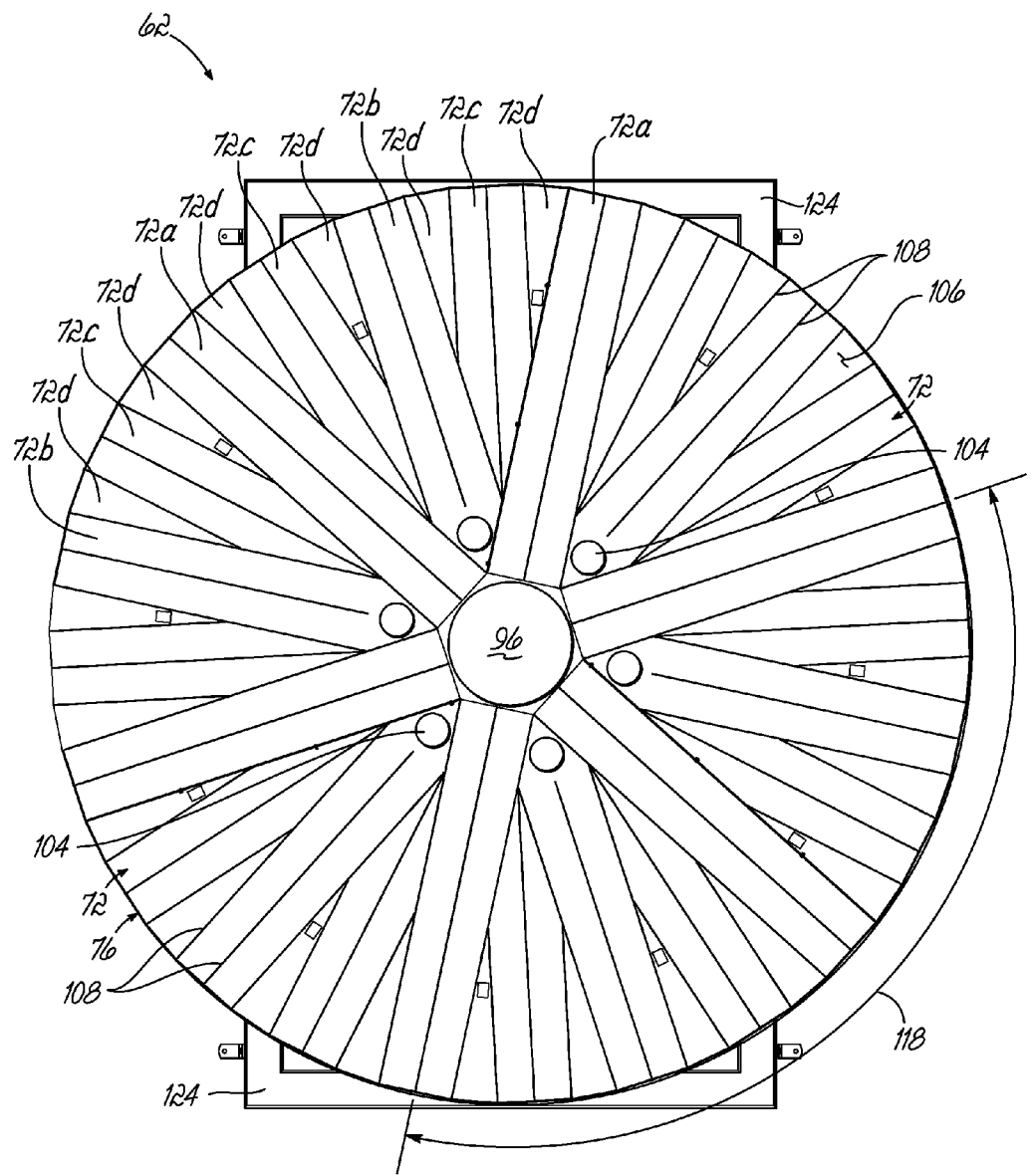
FIG. 5A is a top view of the storage carousel of FIG. 4, illustrating an exemplary layout of one of the shelves.
Figure 5B:
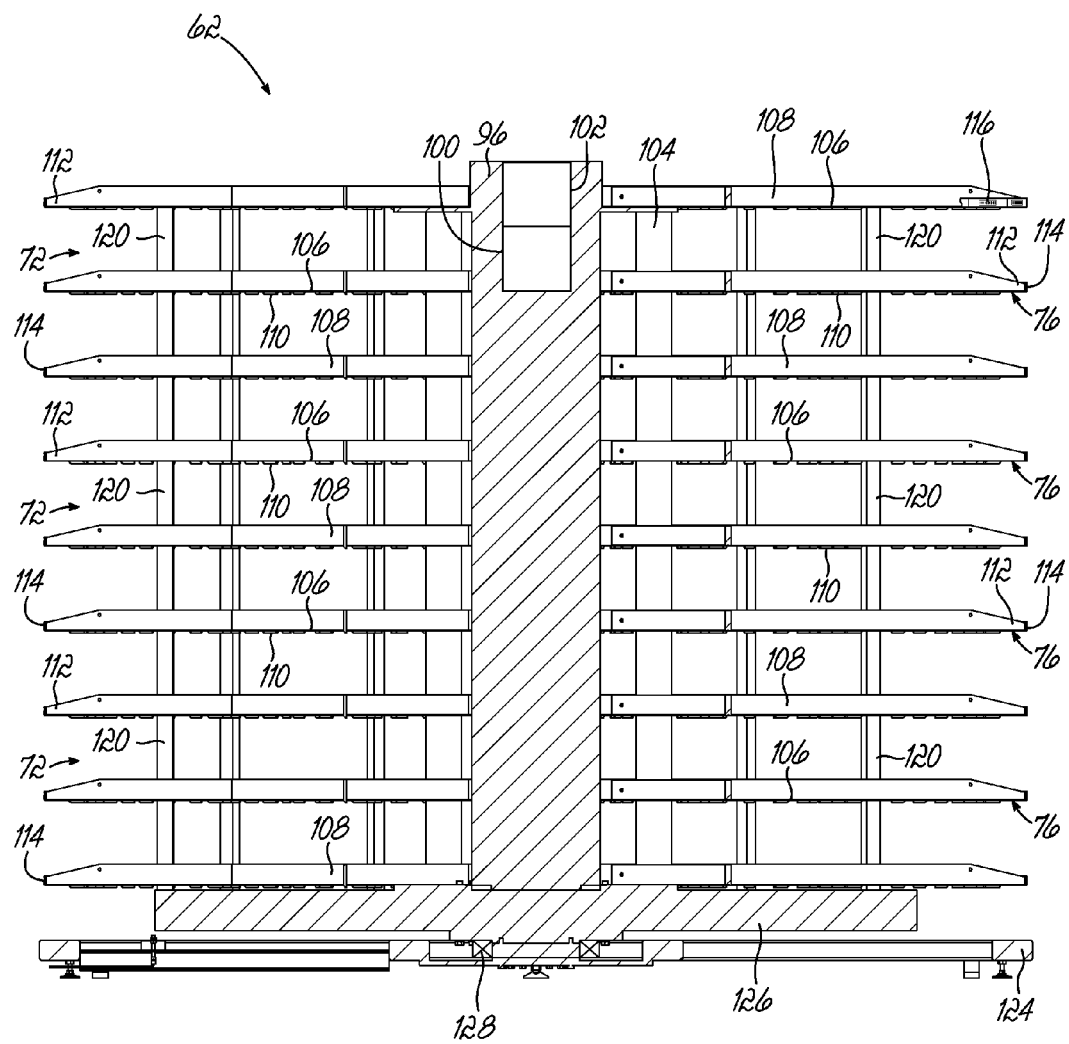
FIG. 5B is a side cross-sectional view of the storage carousel of FIG. 5A, further illustrating assembly features of dividers used on the shelves.
Figure 6:
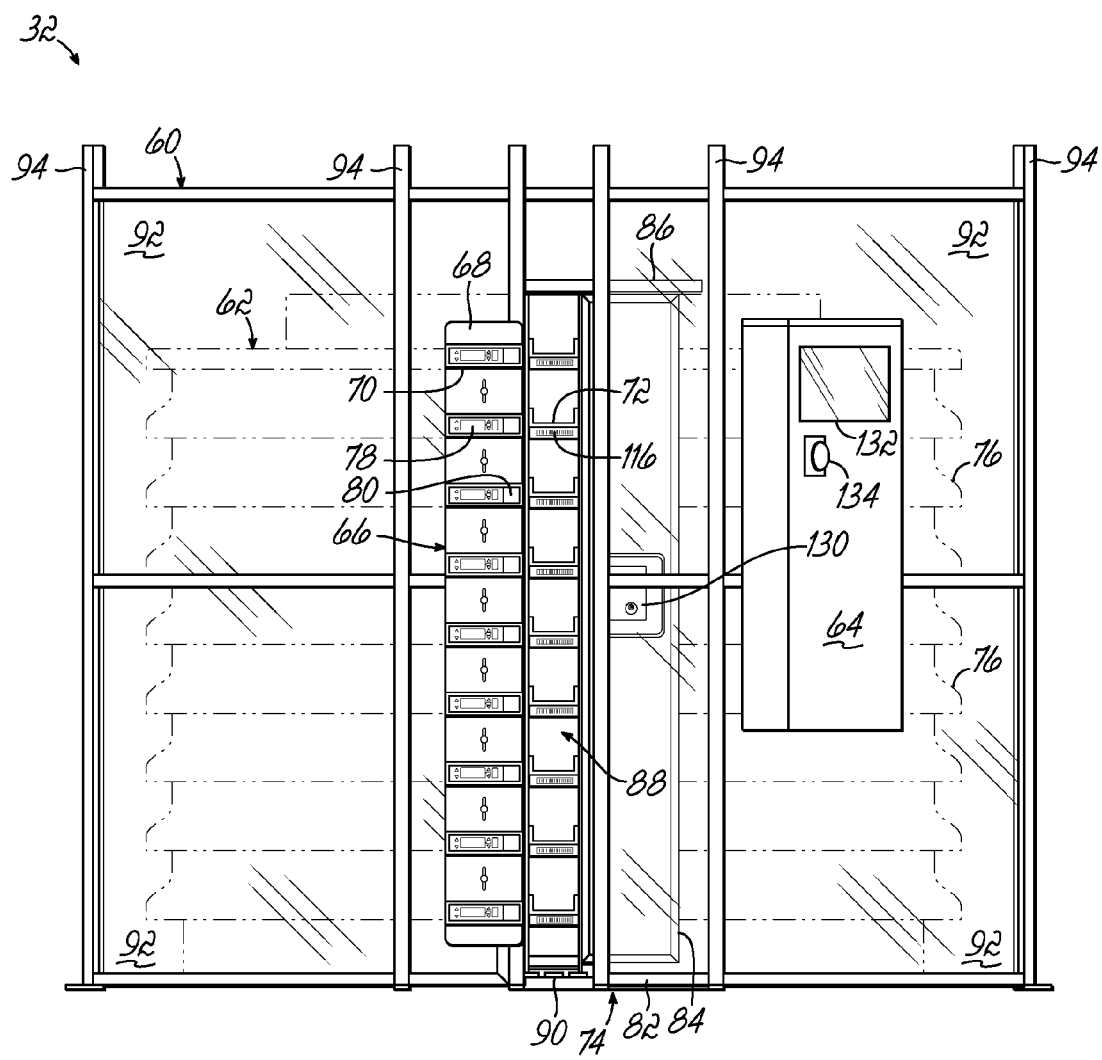
FIG. 6 is a front view of the cage used with the ALV carousel unit of FIG. 3.

The layout and construction of each of the shelves 76 defining the storage bins 72 is further shown with reference to FIGS. 5, 5A and 5B. To this end, each shelf 76 is defined by a horizontal platform 106 and a plurality of divider plates 108 hooked into engagement with the horizontal platform 106. More specifically, the horizontal platform 106 is formed with radially-oriented slots (not shown) configured to receive J-hooks 110 (several of which are shown in FIG. 5B) extending downwardly from the divider plates 108. These J-hooks 110 are aligned with and inserted into the slots and then the divider plate 108 is slid outwardly to lock these J-hooks 110 into engagement with the bottom of the horizontal platform 106. Simultaneously, the leading tip end 112 of the divider plate 108 comes into abutting relation with a rubberized outer peripheral lip 114 on the horizontal platform 106. The outer peripheral lip 114 is shown in FIG. 5B and is also shown in FIG. 6, where it is also shown that each storage bin 72 includes a location barcode 116 mounted on this outer peripheral lip 114 for purposes described below. This process is repeated for each divider plate 108 on the portion of the shelf 76 being assembled, with the smaller length divider plates 108 being inserted first and the longer length divider plates 108 inserted last. In the exemplary embodiment, each shelf 76 is formed in portions of one-third of a shelf 76 (schematically shown by arrow 118 in FIG. 5A), and then these third portions are coupled to one another with screw or bolt fasteners. The entire shelf 76 is then configured for sliding engagement onto the central shaft 96 and the alignment shafts 104.

When the shelf 76 has been fully assembled as shown in FIG. 5A, the horizontal platform 106 and the divider plates 108 have maximized the amount of space within the radially-oriented storage bins 72. To this end, each shelf 76 includes six large storage bins 72a extending directly from the six sides of the hexagonal central shaft 96 of the storage carousel 62. Each of the six large storage bins 72a is sized to receive four product boxes 38 or bulk shipper cases 20. Equally spaced between adjacent large storage bins 72a, a set of six medium storage bins 72b are formed that are sized to receive three product boxes 38. The medium storage bins 72b also include a clearance at the innermost end to receive one of the alignment shafts 104 there through as shown in FIG. 5A. Finally, a set of small storage bins 72c is formed between each medium storage bin 72b and the corresponding two adjacent large storage bins 72a. Consequently, there are twelve small storage bins 72c formed on each shelf 76, each small storage bin 72c being sized to receive one or two product boxes. Each of the storage bins 72a, 72b, 72c receives medical items in blister cards 36 or product boxes 38. It will be understood that additional divider plates 108 may be selectively positioned in the middle of the storage bins 72a, 72b, 72c as shown in FIG. 5A (but not in FIG. 4) to further provide additional storage locations 72 in other embodiments of the invention. The shelf 76 also includes a plurality (24 in the exemplary embodiment) of wedge-shaped bins 72d located between the small storage bins 72c and the adjacent medium and large storage bins 72b, 72a. These wedge-shaped bins 72d may also be assigned a location barcode 116 and filled with loose blister cards 36 not contained in full cases 20, thereby using as much storage space on the horizontal platform 106 as possible.

Thus, each shelf 76 includes 48 positions and storage bins 72 that must be indexed around the storage carousel 62: six large storage bins 72a, six medium storage bins 72b, twelve small storage bins 72c, and twenty-four wedge-shaped storage bins 72d. The shelves 76 are positioned in the same orientation as adjacent shelves 76 such that each of these 48 positions defines one of the vertical storage columns 98 including a stack of storage bins 72 all accessible simultaneously when the position is located at the opening 88 of the door 74. With nine shelves 76 per storage carousel 62, this results in 432 full case sized storage bins 72 on each storage carousel 62 (and over 1200 storage bins 72 in the entire ALV system 30 shown in FIG. 2). In the alternative embodiment described above with intermediate divider plates 108 in the full case sized storage bins 72, the number of storage locations in the storage carousel 72 may be increased to 648 total locations. Ideally, the larger storage bins 72a, 72b will be loaded with medical items that are more frequently used and the smaller storage bins 72c and wedge-shaped bins 72d will be loaded with less-prescribed medical items. This arrangement of medical items on the storage bins 72 will reduce the frequency of when the storage carousel 62 needs reloaded with bulk inventory. Most preferably, the storage carousel 62 is loaded with enough bulk inventory to work through a full day shift and then be reloaded once per day by technicians in overnight or off hours.

The divider plates 108 may be designed with various shapes and sizes, two of which are shown in FIG. 4 and FIG. 5B. Extending in an opposite direction from the J-hooks 110, each divider plate 108 may also include spacing supports 120 configured to extend upwardly into contact with the bottom of the next shelf 76 in series on the storage carousel 62. These spacing supports 120 can be repositioned depending on the particular layout of J-hooks 110 and corresponding slots so that the spacing supports 120 do not abut a J-hook 110. In other embodiments of the storage carousel 62, additional structure may be used to ensure accurate and consistent spacing of the shelves 76, such as structure on the central shaft 96 directly supporting the horizontal platforms 106. Regardless of the method of spacing the shelves 76, adjacent shelves 76 define a height of each storage bin 72 that is sized to receive open bulk shipper cases 20 or product boxes 38. The close fitting of the cases of medical items in the storage bins 72 substantially reduces any movements that may occur while the storage carousel 62 rotates between positions at the door 74, thereby reducing any likelihood of medical items being thrown from the shelves 76.

As shown in FIG. 4, the storage carousel 62 may include a top wall 122 to cover at least a portion of the uppermost shelf 76. The top wall 122 is supported directly by the central shaft 96 and may also be supported by the divider plates 108 of the top shelf 76. This top wall 122 may be omitted in some embodiments. Also shown in FIG. 4, the storage carousel 62 includes a support base 124 configured to be fastened in position on the floor surface to further stabilize the storage carousel 62. The support base 124 is also shown in the cross sectional view of FIG. 5B, where it is further shown that the storage carousel 62 includes a primary support platform 126 holding the central shaft 96 and the bottom shelf 76 and a rotary bearing 128 mounted on the support base 124. The rotary bearing 128 enables rotation of the primary support platform 126 and the remainder of the storage carousel 62 above the primary support platform 126. The motor 102 engages the primary support platform 126 adjacent the rotary bearing 128 and drives the shelves 76 with the aforementioned indexed movement relative to the opening 88 in the door 74 of the cage 60. Therefore, any blister card 36 or product box 38 within the storage bins 72 may be readily brought into position for access by an operator 10 as described in detail below.

With reference to FIG. 6, the portion of the ALV carousel unit 32 adjacent the door 74 is shown in further detail. From this perspective view, the moveable door panel 84 is clearly shown in an open position located behind the stationary door panel 82. The light curtain optical sensor 90 is also shown and includes a plurality of lasers or similar optical sources and receivers (not shown) that form an effective curtain of light that will be interrupted whenever an operator 10 sticks his arm into the opening 88. The optical sensor 90 is operatively connected to the electrical control box 64 and provides a signal that will stop the motor 102 from rotating the storage carousel 62 if such rotation is in progress when the operator 10 inserts his hand through the opening 88. Consequently, the optical sensor 90 ensures the safety of the operator 10 using the ALV carousel unit 32. The optical sensor 90 will also be used to detect movement of operator hands into the carousel area when no transactions (removing stock or replenishing stock) are present. If activity is detected between transactions, flags will be placed on the pick locations that are present at the opening 88. These flags will be used to trigger physical audits to aid in maintaining perpetual inventory accuracy. FIG. 6 also illustrates that the door 74 includes a locking mechanism 130 on the moveable door panel 84 that can be used to lock the moveable door panel 84 in a closed position blocking the opening 88. This closing and locking of the door 74 should be performed anytime the operator(s) 10 stop actively working with the ALV carousel units 32 to prevent any unauthorized access to the storage bins 72 that happen to be located adjacent the opening 88 during periods of non-use. The door 74 is a manually operated door in the exemplary embodiment shown, but it will be understood that the door 74 may be motorized in other embodiments.

FIG. 6 also illustrates the correspondence of the shelves 76 of the storage carousel 62 and the pick modules 70 on the light tree 68 in further detail. In this regard, each of the pick modules 70 is positioned on the cage 60 in order to be at least generally aligned with a corresponding shelf 76 on the vertical storage column 98 of the storage carousel 62 shown accessible through the opening 88. As a result, an operator 10 will not be confused about which shelf 76 to retrieve a desired item from, as the pick module 70 immediately adjacent to that storage bin 72 and shelf 76 will be the one illuminated during such a signal to the operator 10. Thus, each pick module 70 is selectively illuminated according to pick indicator logic described in further detail below. When the storage carousel 62 rotates to a position with a storage bin 72 having a medical item to be retrieved facing towards the opening 88, the corresponding pick module 70 will prompt the operator 10 to go to the intended storage bin 72 and pick the indicated number of blister cards 36 or product boxes 38. The operator 10 can pick multiple items at once or one at a time, as the operator 10 indicates when any number of items has been removed by pressing buttons on the pick modules 70. If medical items are to be pulled from multiple shelves 76 at a particular position, all of the pick modules 70 will illuminate simultaneously in the exemplary embodiment. Until the operator 10 extinguishes all of the illuminated pick modules 70 to indicate removal of the appropriate number of blister cards 36 and product boxes 38, the storage carousel 62 will not be rotated to the next position with picks to be retrieved. Similar to the optical sensor 90, the pick modules 70 are also operatively connected to the other elements of the ALV carousel unit 32 such that the number of items to retrieve indicated on the display of the pick module 70 (as decremented by actions of the operator 10) will be communicated to the pharmacy host server 56 so that the server 56 keeps track of what medical items have been picked for each customer order.

The controller box 64 (also referred to as an electrical control box) may interface with the storage carousel 62 via a drive controller (not shown in FIG. 6) incorporated with the electrical control box 64, where the drive controller is configured to control the motor 102 that rotates the storage carousel 62. The electrical control box 64 may also include a human machine interface HMI panel 132 configured to display operating status of the mechanical elements such as the motor 102 controlled by the drive controller. The electrical control box 64 also includes an emergency stop button 134 for stopping all operations of the storage carousel 62 when necessary for any reason. The HMI panel 132 and the emergency stop button 134 are located at a height that is easily reachable for nearly all operators 10.

Figure 7:
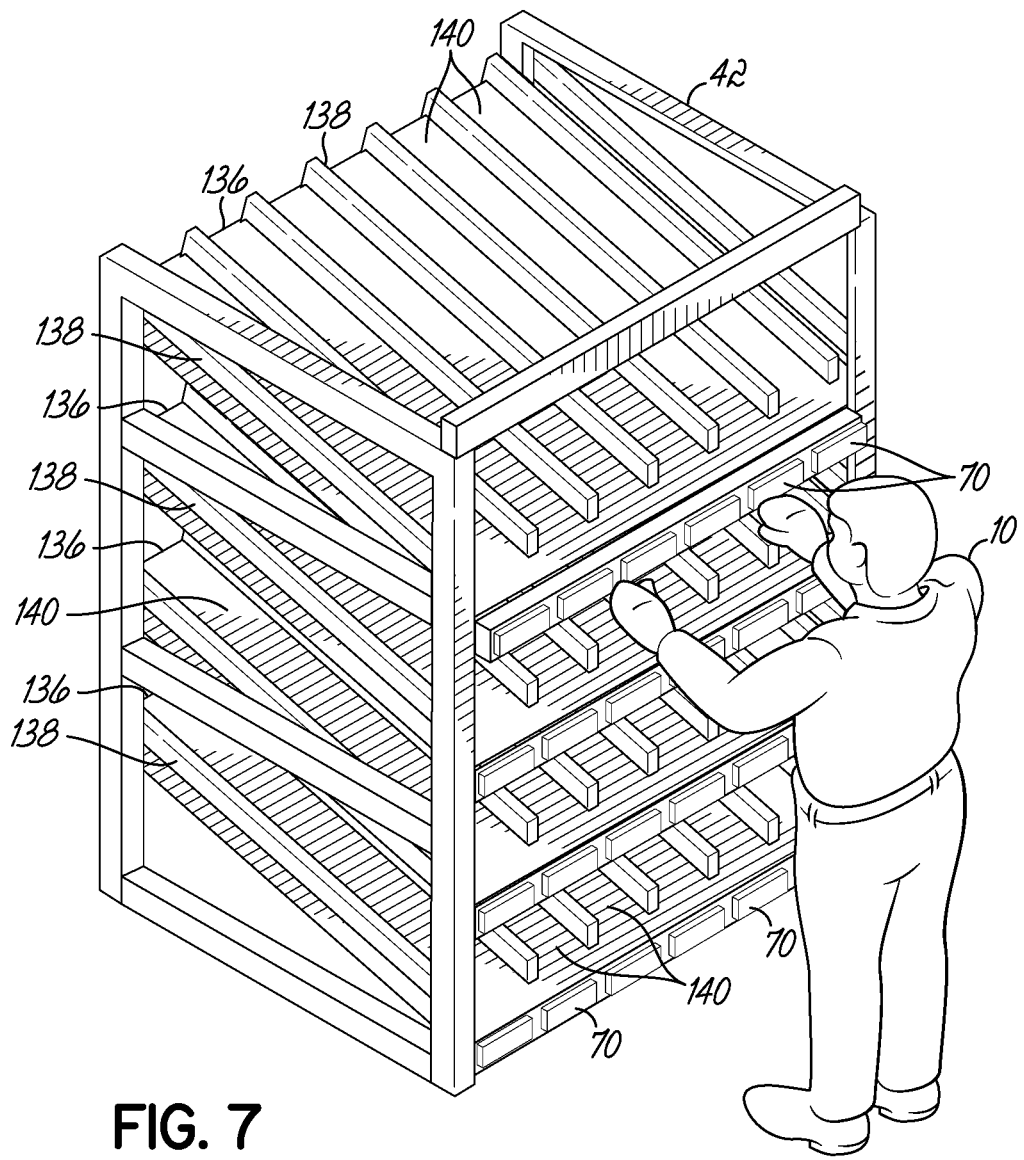
FIG. 7 is a perspective view of a pick-to-light storage rack of FIG. 2 used in conjunction with the ALV carousel units.

A representative pick-to-light rack 42 of the pick-to-light system 40 is shown in FIG. 7. Each of the pick-to-light racks 42 includes a bay controller (not shown) and multiple shelves 136 arranged in levels. Each of the shelves 136 is partitioned by dividers 138 to define multiple bins or inventory locations 140 that are within arms-reach of a technician and stocked with one or more bulk shipper cases 20 of blister cards 36 or product boxes 38. Each product 36, 38 may be characterized by a unique drug stock-keeping unit or SKU. More than one inventory location/bin 140, typically adjacent bins 140, in the pick-to-light racks 42 can hold bulk shipper cases 20 holding products 36, 38 with the same drug SKU for more often-used or faster moving medical items, which are managed as a single unit by the ALV system 30. However, most drug SKUs have a single inventory location on the shelves 136 of the pick-to-light racks 42. The vertical position and inclination angle of the shelves 136 in the pick-to-light racks 42 may be adjustable. The pick-to-light racks 42 may be arranged to locate specific inventory locations 140 for products 36, 38 of faster moving drug SKUs within easier reach for most operators 10, or closer to the product inlets 34 of the ALV machine 44.

In a manner not shown herein, each inventory location 140 in the pick-to-light racks 42 has a dedicated pick-to-light module 70 with a pick face that includes an indication light, one or more buttons 80, and an alphanumeric display module 78. The alphanumeric display 78 indicates to the operator 10 the number of products 36, 38 to be picked for an order, and the buttons 80 permit the operator 10 to adjust the quantity up, or down, if there are inventory issues. The adjustments provide a means for the operator 10 to update the database of the pharmacy host server 56 with real-time, accurate inventory counts of products 36, 38. Thus, the pick modules 70 used with the pick-to-light racks 42 follow the same logic as those pick modules 70 used with the storage carousels 62. Each of the pick-to-light racks 42 may include other types of pick-to-light modules, such as an order control module, that are operated under the control of the bay controller.

As briefly described above, orders in the form of pick requests are communicated from the pharmacy host server 56 to the ALV system 30. As discussed above, the pick requests are stored for logical grouping based on user-defined parameters and retrieval. The logical grouping process results in pick batches for the operator to pick from the ALV carousel units 32 and from any pick-to-light racks 42 that may be located in the pick-to-light system 40. Each pick batch can contain one or more products in the form of blister cards 36 and product boxes 38 destined for a placement into the same customer order or grouping of customer orders. The operator 10 then collects each of the picks from the ALV carousel units 32 and any required from the pick-to-light racks 42 as indicated by the illumination of pick modules 70 on each of these elements. The operator 10 will understand that a pick batch has been completed when all of the pick modules 70 have been extinguished. A new order button (not shown) may then be actuated to start a new order, after the operator 10 has delivered the previous batch to the ALV machine 44 at the product inlets 34.

The operator 10 can place each of the picks from the ALV carousel units 32 into a tote or container 50 to carry those picks to the product inlets 34. These totes may be referred to as a work in process (WIP) tote or shipping (SHP) tote if the items sorted into the tote 50 were sorted by a single facility, and these totes may be referred to as an aisle (ASL) tote if the medical items in the tote 50 are sorted to be associated with multiple facilities. Following the collection of medical items into the tote 50, the process of individually labeling the items can continue at the ALV machine 44 as described in detail below.

Figure 8:
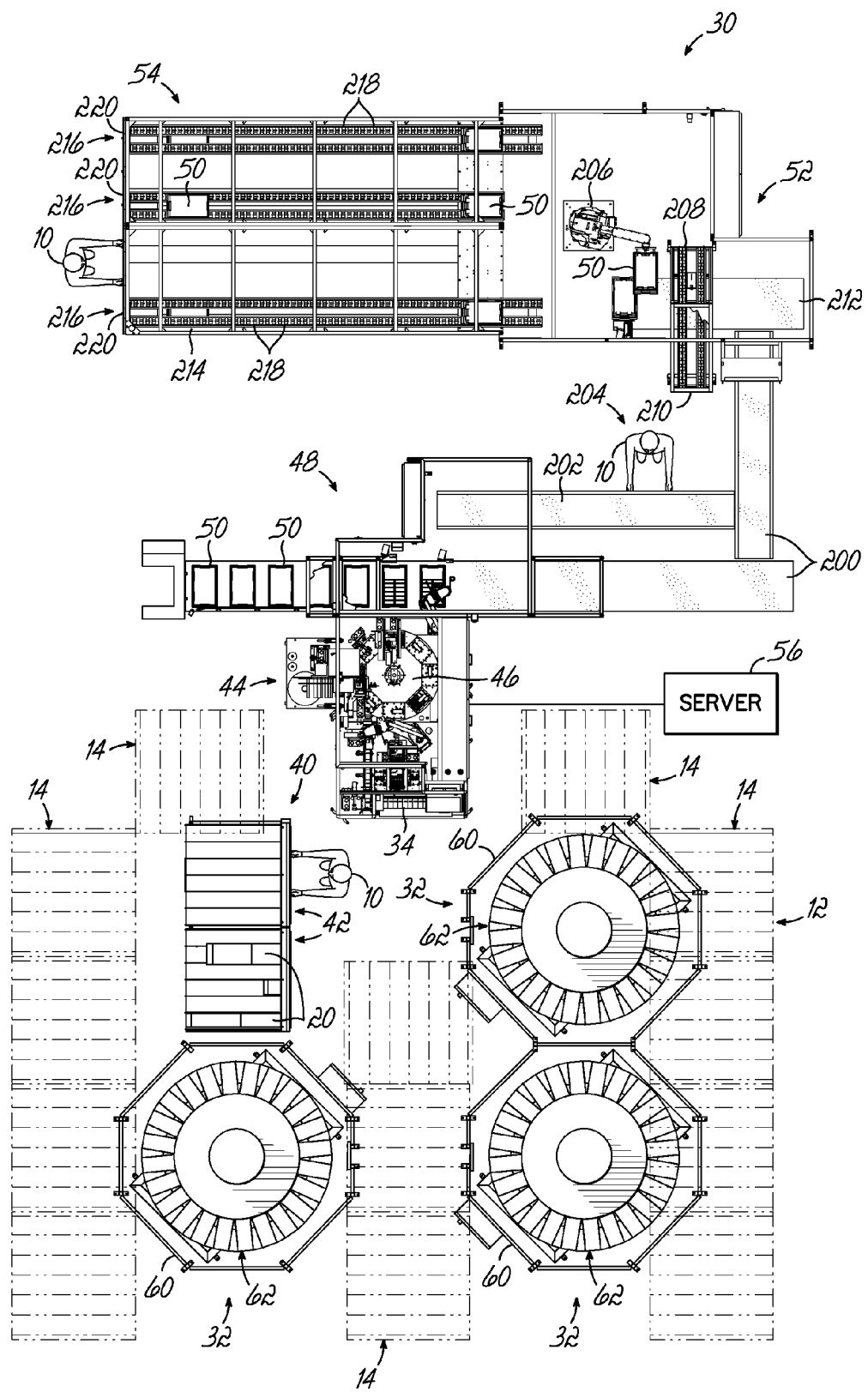
FIG. 8 is a top schematic view of the ALV system of FIG. 2 with the conventional pick-to-light system of FIG. 1 overlaid in phantom to compare this system with the plurality of ALV carousel units.

With reference to FIG. 8, the ALV system 30 is illustrated from a top plan view as previously shown in FIG. 2, but with the previous version of the pick-to-light system 12 shown in phantom and overlaid over the pick-to-light system 40 of the current invention. As shown in FIG. 8, the pick-to-light system 40 requires about half of the floor space required for the conventional pick-to-light system 12. This tighter configuration reduces the amount of steps an operator 10 needs to take when collecting all picks for a batch. Moreover, when using an ALV system 30 including a series of ALV carousel units 32 such as the plurality shown in the exemplary embodiment, an operator 10 has access to well over 1000 distinct storage locations/bins 72, 140 that may contain distinct medical items and products for use in forming pre-sorted batches to label and verify. These 1000 or more storage locations/bins 72, 140 are served by 75 pick modules 70 that indicate where to pick items for a particular batch for a customer order. In contrast, the conventional pick-to-light system 12 described above includes only 312 product storage locations, each requiring a separate pick module (e.g., 312 pick modules at 312 product storage locations). Thus, the use of the ALV carousel units 32 in the pick-to-light system 40 of the exemplary embodiment provides many more product storage locations 72, 140 with significantly fewer pick modules 70 required, thereby saving on system cost and overall reliability.

Figure 9:
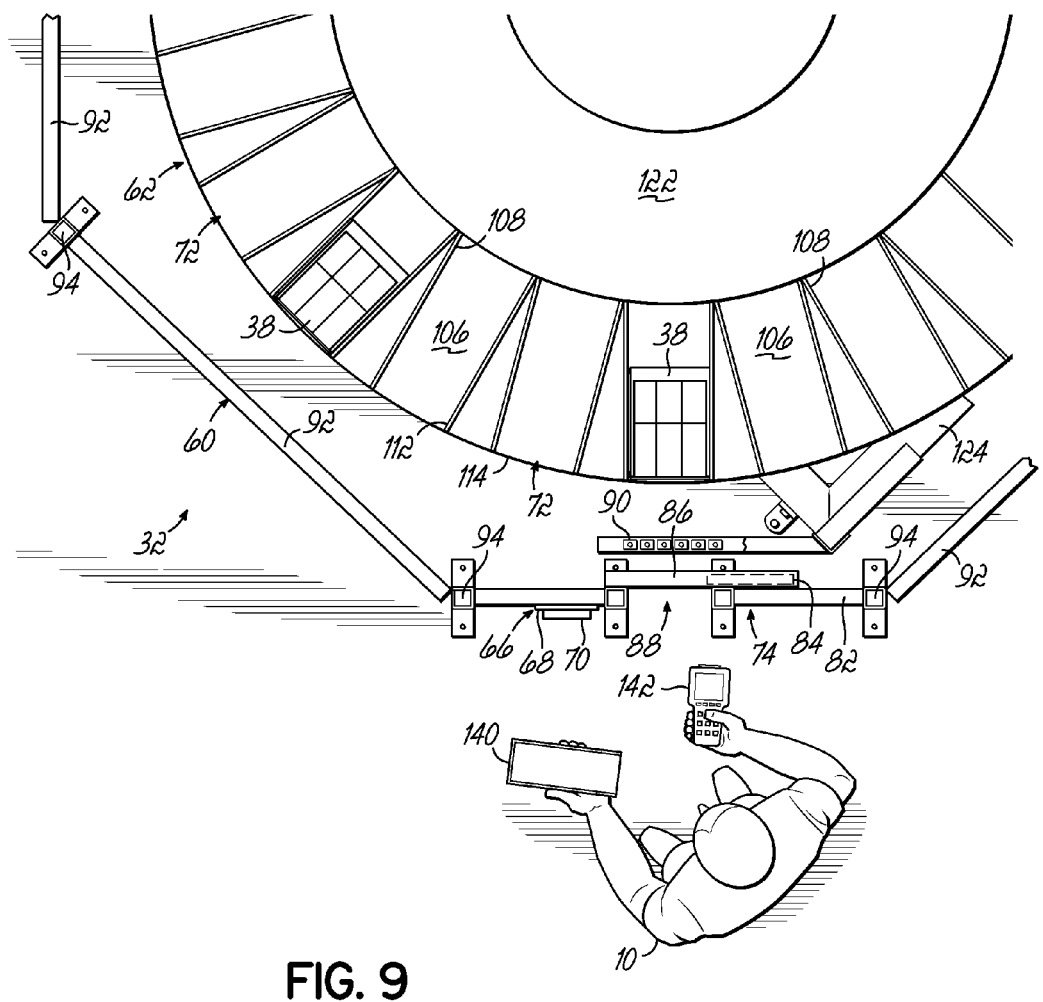
FIG. 9 is a top view of a portion of the ALV carousel unit of FIG. 3, showing an operator working at the ALV carousel unit.
Figure 9A:
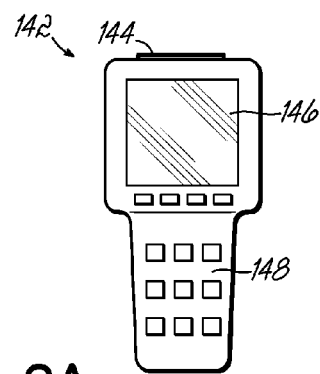
FIG. 9A is a top view of a hand scanner used by the operator of FIG. 9.

With reference to FIG. 9, an operator 10 is shown working at the ALV carousel unit 32. The operator 10 is holding a product box 38 in one hand and a manual scanner 142 in the other hand. As described in further detail below, the manual scanner 142 is a barcode scanner that may be used during operations performed at the ALV carousel unit 32. As shown in FIG. 9A, the manual scanner 142 includes a barcode scanner 144 on a free end and a small display screen 146 and keypad 148 on the top side. The operator 10 uses the manual scanner 142 to scan location barcodes 116 and product labels on medical items that are to be placed into storage bins 72 or retrieved from storage bins 72. The manual scanner 142 is most often used during an inventory replenishment or query process described in further detail below, but it may be used during the collection of picks in batches as well in some embodiments.

Figure 10:
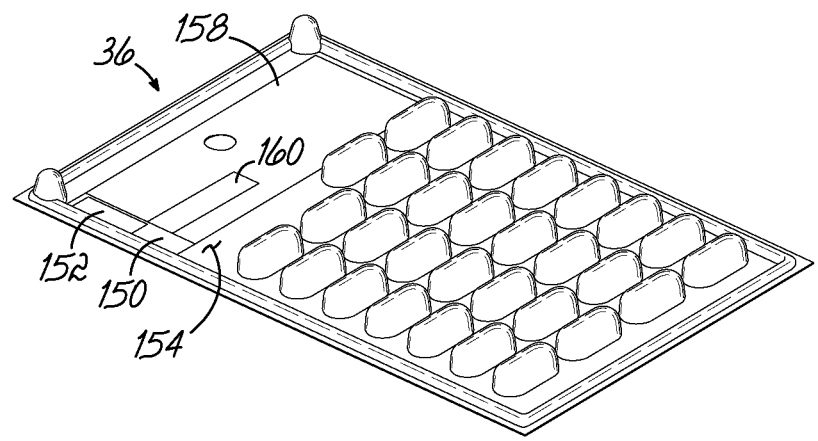
FIG. 10 is a perspective view of a blister card form factor used with the ALV system of FIG. 2.
Figure 11:
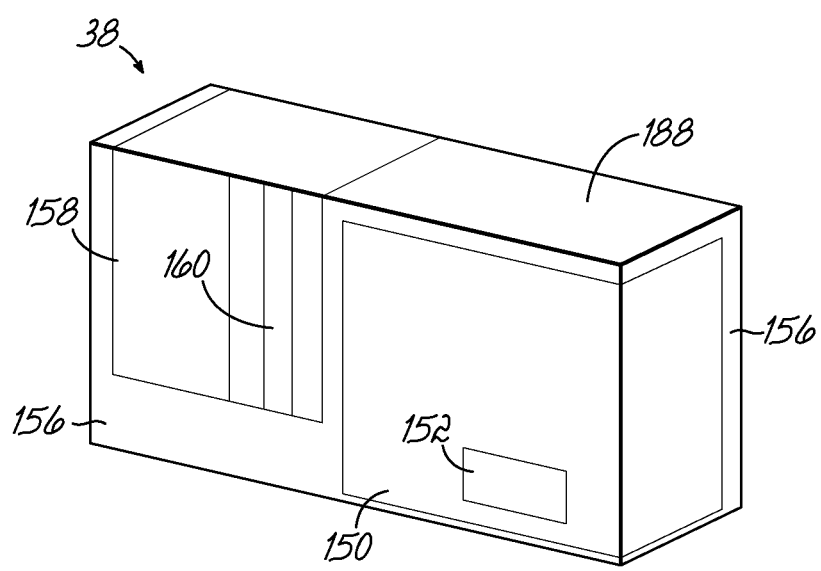
FIG. 11 is a perspective view of a product box form factor used with the ALV system of FIG. 2.

With reference to FIGS. 10 and 11, the product form factors of a blister card 36 and a product box 38 are shown in further detail. Each type of product 36, 38 includes a product label 150 having a product barcode 152 that reflects the contents of the product 36, 38. Groups of products 36, 38 in a common bulk shipper case 20 supplied to the pharmacy typically share the same mutual product barcode 152. The product barcode 152 may be printed directly on a surface of the product 36, 38 or, alternatively, may be printed on the product label 150 as shown in FIGS. 10 and 11. The product barcode 152 is positioned on the products 36, 38 of the same form factor in a consistent manner (i.e., at substantially the same location on the products 36, 38) so that it can be brought into the field of view of readers used by the ALV system 30 to read the product barcode 152. To that end, as shown in FIG. 10, the product barcode 152 on each of the blister cards 36 may be positioned on a front surface 154 near one corner of the blister card 36 and inset slightly from the card perimeter. As shown in FIG. 11, the product barcode 152 on each of the product boxes 38 may be positioned on one of two sidewalls 156 of the product box 38. Regardless of the form factor, the positioning of the product barcode 152 on the products 36, 38 is chosen such that the product barcode 152 is not obscured or obstructed after a patient label 158 is applied to the product 36, 38 by components within the ALV system 30.

The patient label 158 (outlined schematically in FIGS. 10 and 11) is printed on conventional label stock and includes an adhesive backing for adhesively bonding to the product 36, 38. A patient barcode 160, which encodes information relating to the prescription and the patient end consumer, is situated within a given spatial window or footprint inside the perimeter of the patient label 158. The ALV system 30 is tolerant of slight inaccuracies in the precise location of the patient barcode 160 on the patient label 158 and of the patient label 158 on the product 36, 38 for purposes of reading the patient barcode 160. The positioning of the patient barcode 160 on the labeled products 36, 38 is reproducible to an extent necessary for the field of view of readers used by the ALV system 30 to read the patient barcode 160. The patient label 158 may further include human-readable information relating to the drug or pharmaceutical contained in the product 36, 38 and/or the customer for the pharmaceutical or other medical item contained in the product 36, 38. As described in further detail below, the patient label 158 is printed, applied, and verified to match the product label 150 at the ALV machine 44.

Figure 12:
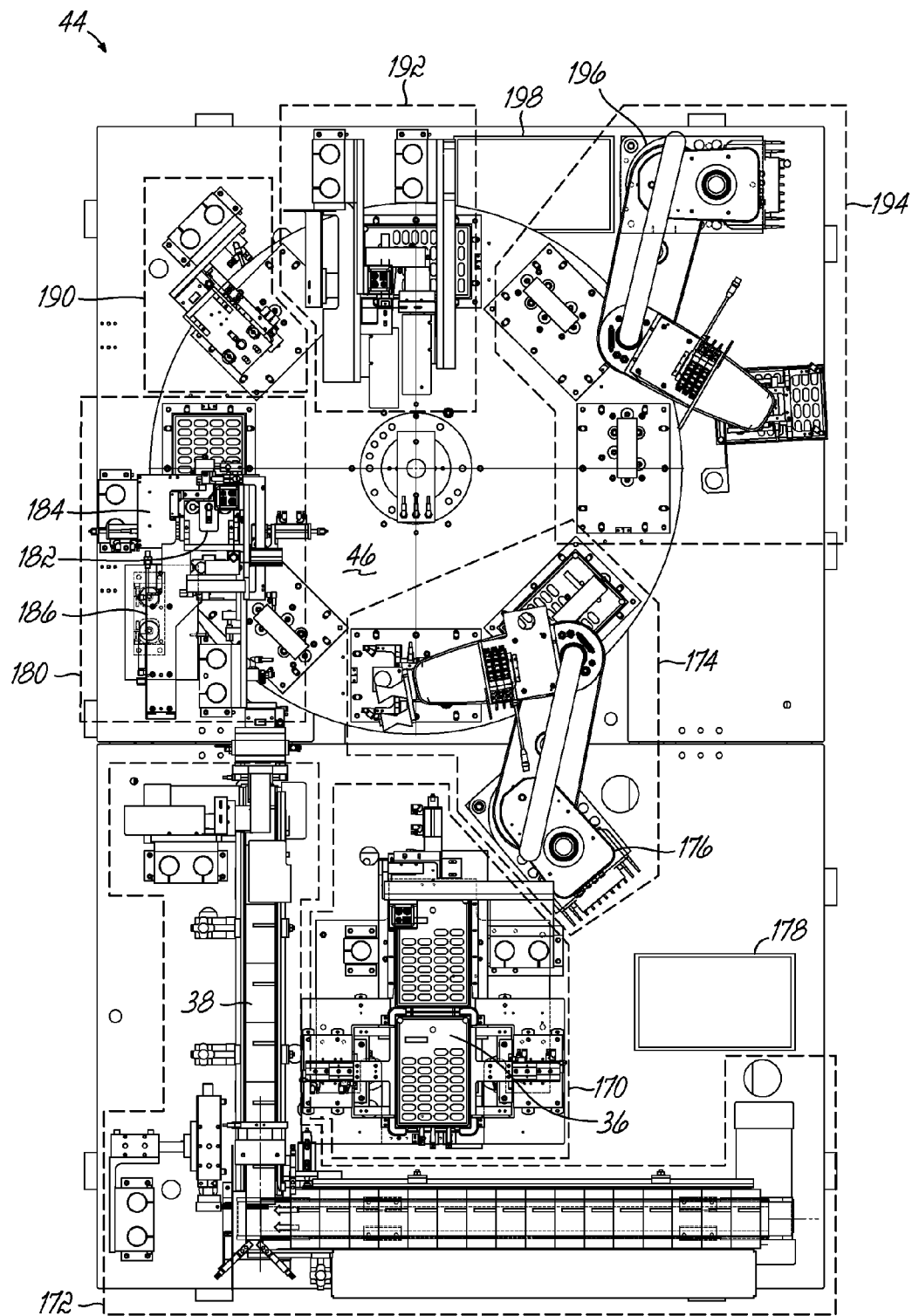
FIG. 12 is a top plan view showing the layout of the ALV machine and turntable used with the ALV system of FIG. 2.

Referring now to FIG. 12, the ALV machine 44 includes both a card loading station 170 and a box loading station 172 to define the product inlets 34 for receiving the products 36, 38 pulled by an operator 10 from the racks 42 and ALV carousel units 32 of the pick-to-light system 40. The card loading station 170 and box loading station 172 are each configured to read the product barcode 152 (FIGS. 10 and 11) on the associated type of products (i.e., blister cards 36 and product boxes 38) to verify and track the products 36, 38. This verification task is achieved while delivering the products 36, 38 in an organized manner to a transfer station 174, which includes a transfer arm in the form of a robot 176 for transferring the products 36, 38 to designated locations on a rotary or dial conveyor 46. The robot 176 also transfers the products 36, 38 to a first reject bin 178 (instead of the dial conveyor 46) under certain conditions, such as when a product 36, 38 cannot be verified. Thus, aspects of the card loading station 170 and box loading station 172, together with the transfer station 174, serve as a first product verification and rejection (PVR1) station.

The dial conveyor 46 rotates to deliver or bring the products 36, 38 to a labeling station 180. At this station, the ALV machine 44 prints the patient labels 158 (FIGS. 10 and 11) having patient-specific information in the form of the patient barcode 160, verifies that the patient barcode 160 is printed on each patient label 158, and applies each successfully-verified patient label 158 to the corresponding product 36, 38. More specifically, a label printer 182 associated with the ALV machine 44 prints the patient labels 158 to apply the patient-specific information. A label applicator 184 verifies the patient barcode 160 and applies the associated patient label 158 to the corresponding product 36, 38. Patient labels 158 that fail verification are applied to label reject device 186 rather than to one of the products 36, 38. Thus, the labeling station 180 serves as a label print, verify, and apply (LPVA) station.

When products 36, 38 in the form of product boxes 38 are being processed, the labeling station 180 applies the associated patient label 158 to a front surface 188 (FIG. 11, viewed from above and looking downwardly) of each product box 38. The patient label 158 has a width greater than that of the front surface 188 such that projecting portions of the patient label 158 extend outwardly above the sidewalls 156 when the patient label 158 is applied to the front surface 188. To complete the label application process, the dial conveyor 46 further rotates to bring the product box 38 to a label wipe station 190 that pushes these projecting portions flat onto the opposed sidewalls 156 of the product box 38. The blister cards 36 are not processed by the label wipe station 190 because the patient labels 158 are initially applied entirely flat onto the front surface 154 (FIG. 10) of this form factor.

The next station associated with the circular workflow path of the dial conveyor 46 is a vision inspection station 192 that performs another verification step. At the vision inspection station 192, the ALV machine 44 re-verifies both the product barcode 152 on the product label 150 and the patient barcode 160 on the patient label 158. If either of the barcodes 152, 160 cannot be read or do not match/correlate with product tracking data, the product 36, 38 is flagged as a reject. If the barcodes 152, 160 do match/correlate with product tracking data, the product 36, 38 is flagged as an accepted item. The dial conveyor 46 then brings the product 36, 38 to an unloading station 194. A robot 196 at the unloading station 194 transfers the products 36, 38 flagged as rejects into a second reject bin 198 and transfers the products 36, 38 flagged as accepted items into one of the containers 50 on the tote conveyor system 48. Thus, the vision inspection station 192 and unloading station 194 collectively serve as a second product verification and rejection (PVR2) station.

Figure 13:
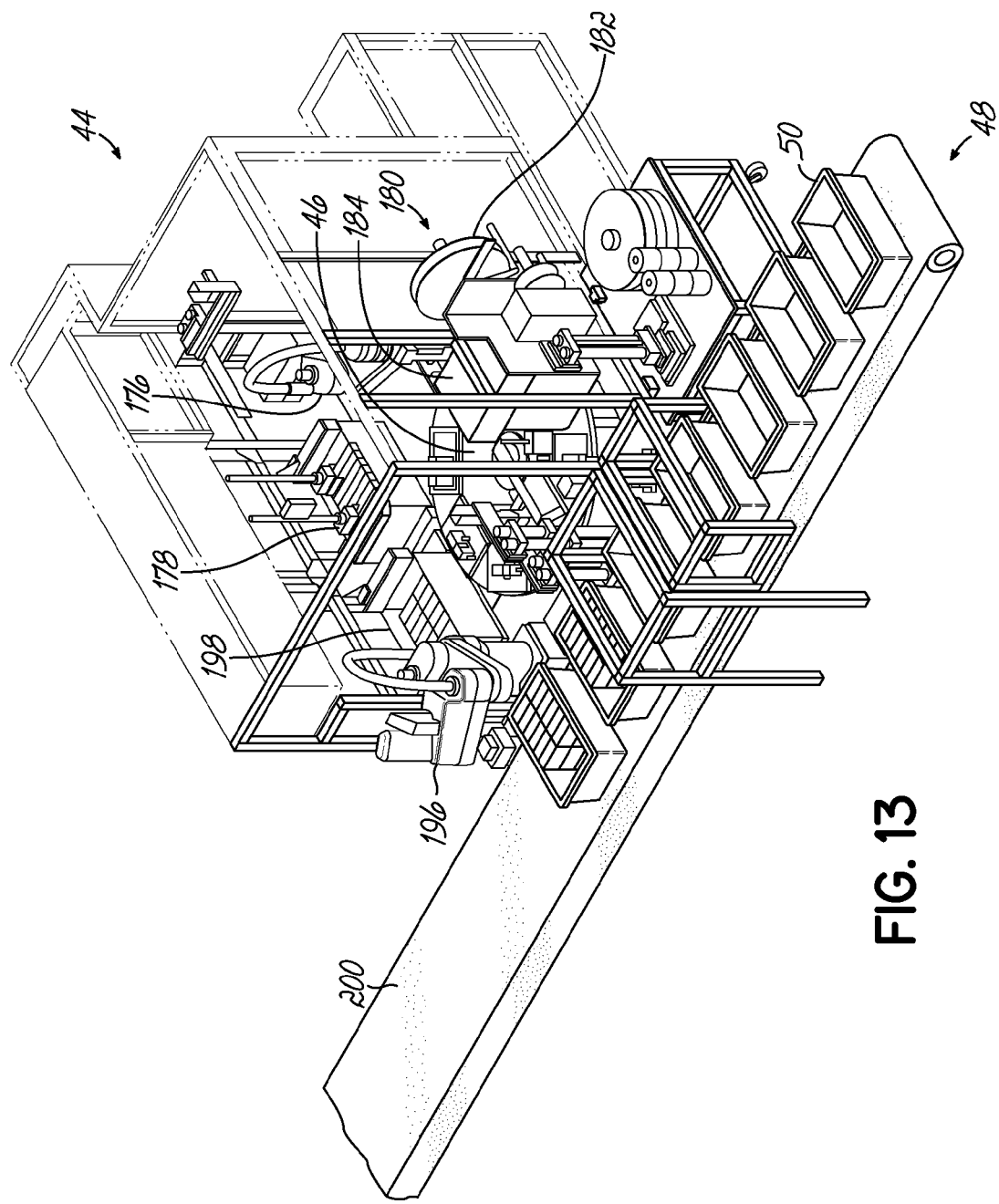
FIG. 13 is a perspective view of the ALV machine and a portion of a tote conveyor machine used with the ALV system of FIG. 2.
Figure 14:
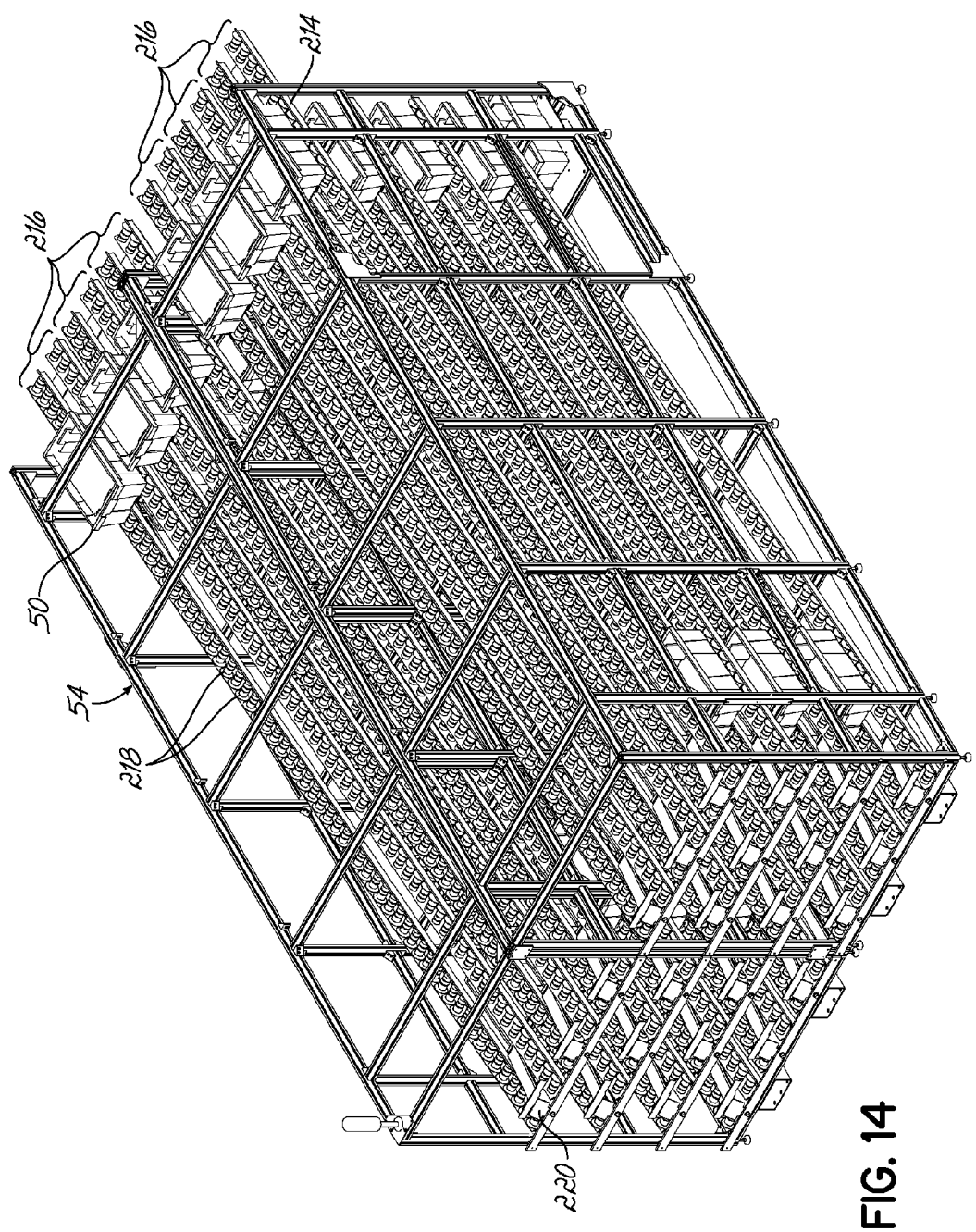
FIG. 14 is a perspective view of a tote rack used with the ALV system of FIG. 2.

The tote conveyor system 48 is further shown with reference to FIGS. 8 and 13. The tote conveyor system 48 is closely integrated with the operation of the ALV machine 44 and sends the totes/containers 50 filled with verified and labeled products 36, 38 along a main conveyor 200 to the tote handling system 52. The tote conveyor system 48 also includes a parallel conveyor 202 so that the filled containers 50 can alternatively be sent to an audit station 204 whenever an audit is desired for quality assurance. At the audit station 204, an operator 10 uses a hand-held or manual scanner 142 and operator's interface to verify the contents of the container 50 before passing the container 50 to the tote handling system 52. A tote load robot 206 in the tote handling system 52 places the containers 50 onto a tote rack 54 or, when an audit is to be performed, onto a tote return conveyor 208 leading to an escapement 210 where an operator 10 at the audit station 204 can pick up the container 50. Thus, a filled container 50 may be transferred to the audit station 204 by either the tote conveyor system 48 or the tote handling system 52.

In one specific embodiment, the tote load robot 206 is a six-axis Adept Viper™ robot available from Adept Technologies, Inc. The tote load robot 206 is configured to pick the containers 50 up and place them either onto the tote return conveyor 208 for delivery to the audit station 204 as described above or onto the tote rack 54 for temporary storage. The tote rack 54 includes shelves 214 divided into separate lanes 216 for storing the containers 50. The lanes 216 are inclined from the front of the tote rack 54, which is accessible by operators 10, to the rear of the tote rack 54, which is accessible by the tote load robot 206. Because the lanes 216 each comprise a plurality of rollers 218, containers 50 deposited by the tote load robot 206 are able to travel along the lanes 216 to the front of the tote rack 54. Stop panels 220 are positioned at the front of the tote rack 54 to prevent the containers 50 from falling off the shelves 214. The operators 10 can then move the totes or containers 50 from the tote rack 54 directly to the shipping containers for end consumers in downstream processing.

Although only one ALV system 30 is shown, a pharmacy can house multiple ALV systems (not shown) each identical or substantially similar to ALV system 30. The ALV system 30 may constitute stand-alone stations in a non-integrated pharmacy, each having their own tote conveyors systems 48 and tote handling systems 52, or components of an integrated (i.e., automated) pharmacy in which the individual ALV systems 30 are linked together by a shared tote conveyor system 48 and/or tote handling system 52. In the latter instance, multiple ALV systems 30 inside the same pharmacy may be logically connected to one of the ALV systems 30 (designated as the primary ALV system 30) via a communications channel, such as an Ethernet communications channel, and physically connected to the tote conveyor system 48 and/or tote handling system 52 shared by the multiple ALV systems 30. The AOM control system of the primary ALV system 30 may be used to control one or more of the additional ALV systems 30 housed in the pharmacy.

Thus, the medical items needed for an entire pre-sorted batch of medical items used in a particular customer order are brought to the operator for labeling and verification without requiring the operator to walk along multiple aisles of storage racks to retrieve and pre-sort the batches from bulk inventory. The ALV carousel units force transactions on a batch-by-batch basis to limit the number of incorrect products that may be retrieved by an operator when preparing the batches for labeling and verification. These medical items can be labeled with patient labels and verified all at once upon retrieval from the storage carousels by placing the pre-sorted batches of medical items into the ALV machine. This process enables labeling on demand and significantly fewer human touches required to retrieve, label, and process the products in a customer order for shipping to the end consumer (in some further embodiments not shown, another robot at the pick-to-light system 40 could be used to pull the medical items from the ALV carousel units 32 and the pick-to-light racks 42, thereby removing additional human touches). This on demand labeling ensures that all medication order changes, details, label instructions, and other information are up to date at the latest possible time before applying the patient label to the product. In addition, this on demand labeling enables checking for conditions that would prompt pharmacist re-verification of the clinical order such as drug contra-indications, allergen alerts, and product changes that may arise in the time period immediately before printing and applying the patient label to the product. Only one correct patient label is printed and applied to each product in the ALV machine, which reduces waste of label material (and the associated costs of incinerating or otherwise disposing of private patient information). Furthermore, the accurately pre-sorted totes of medical items can be scanned and handled on a tote-by-tote basis (for WIP and SHP totes as described above, as ASL totes require further scanning actions to separate the medical items into customer orders) downstream of the labeling and verification process rather than requiring sorting into separate shipping bags during downstream processing. This process can therefore improve the number of products labeled and verified over a traditional manual process from 1 product per 1-3 minutes to about 18 products per minute.

The ALV system of the current invention is also advantageous because it provides an adequate number of storage bins or locations for all of the products that may be filled by a pharmacy that use blister cards or product boxes as the packaging mechanism. Thus, the manual process of printing pick tickets and using NPTL batch preparation processes as used with previous versions of ALV systems is not required with the current ALV system. This high-density storage of the products reduces the amount of space needed for the ALV system, which could enable the ALV system 30 to be installed in smaller pharmacies where appropriate. The ALV system 30 also enables leveraging of "First In, First Out" (FIFO) inventory control by directing the operator to pick from the oldest stock in the storage carousels, thereby reducing the amount of product waste. The ALV system 30 also enables leveraging of "First Expired, First Out" (FEFO) inventory control by directing the operator to pick from the stock that has the earliest expiration dates in the storage carousels. Furthermore, the significantly reduced number of pick modules required by the ALV system improves the reliability and reduces the cost of the pick-to-light system and therefore also the ALV system.

Figure 15:
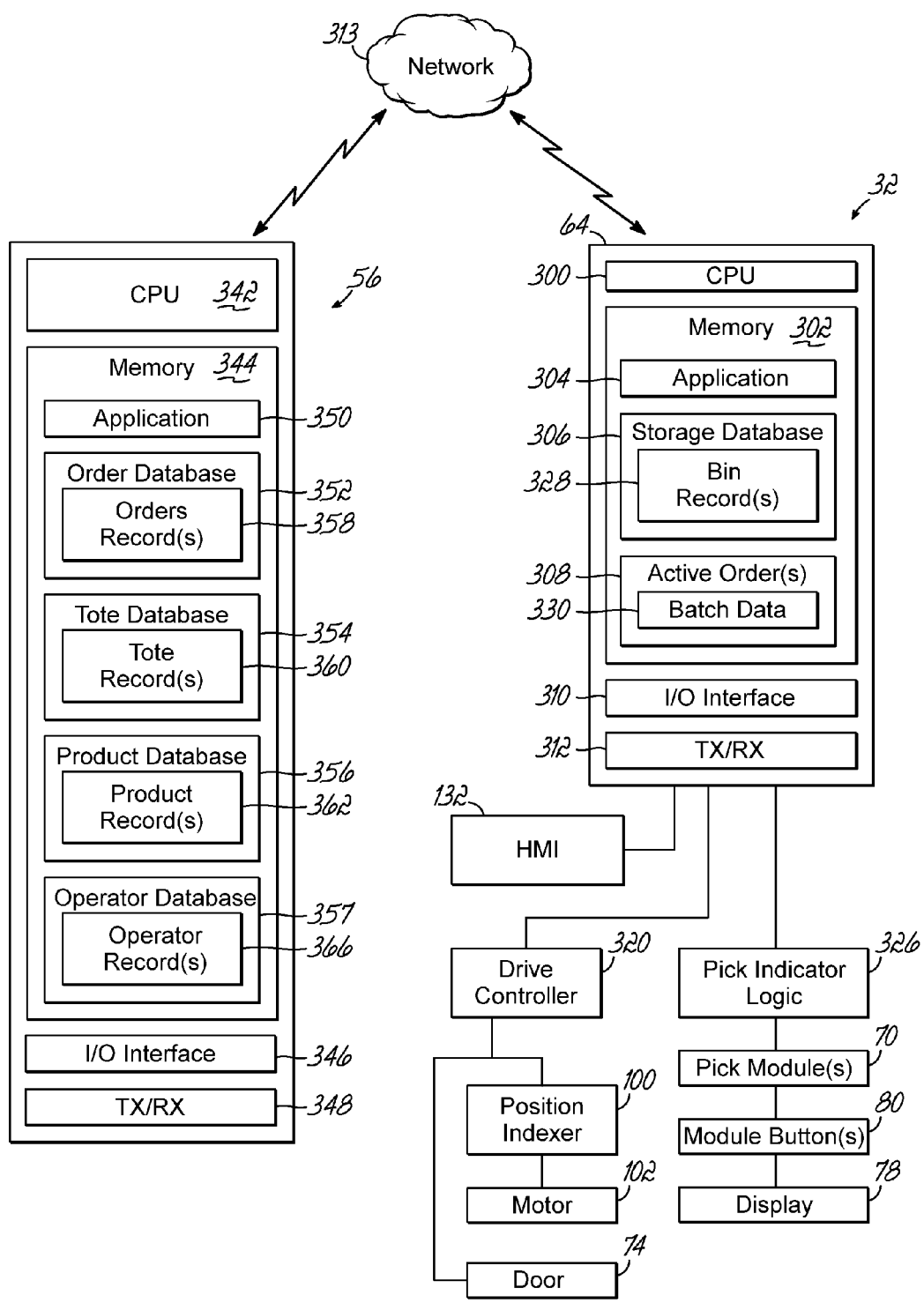
FIG. 15 is a block diagram illustrating components of an embodiment of the ALV carousel unit of FIG. 3 and a pharmacy host server used with the ALV carousel unit.

FIG. 15 provides a block diagram illustrating components of the ALV carousel unit 32 and components of a pharmacy host server 56 consistent with some embodiments of the invention. As shown, a controller box 64 of the ALV carousel unit 32 includes one or more processors (illustrated as 'CPU') 300 for executing one or more instructions to perform and/or cause components of the ALV carousel unit 32 to perform one or more operations consistent with embodiments of the invention. The controller box 64 includes a memory 302, where the memory 302 includes an application 304 and the memory 302 may also store one or more data structures 306, 308. Application 304 may generally comprise program code that when executed by the processor 300 facilitates retrieving, labeling and/or verifying products for filling a customer order. Furthermore, the controller box 64 includes an input/output ("I/O") interface 310 configured to output data to and receive data from one or more peripherals in communication with the ALV carousel unit 32, a network interface controller ("Tx/Rx") 312 configured to transmit and receive data over a communication network 313, and/or a machine interface ("HMI") 66 that may include one or more peripherals for outputting data to the operator 10 in an understandable format and receiving input data from the operator, including, for example, a display and/or an input peripheral (for example, one or more buttons, such as emergency stop button 134 and/or hand scanner 142).

The ALV carousel unit 32 generally includes a carousel drive controller 320 configured to control a motor 102 connected to a rotatable storage carousel 62 to rotate the storage carousel 62 a determined amount such that a storage bin 72 may be aligned to the opening 88 of a cage 60 surrounding the storage carousel 62 (the opening 88 may be referred to as a pick location). In addition, the carousel drive controller may operate a door 74 associated with the cage 60. The ALV carousel unit 32 generally includes pick indicator logic 326 configured to selectively control one or more pick modules 70 to thereby indicate to the operator particular storage bins 72 from which to retrieve products as well as a quantity of the product which the operator is to retrieve via the associated display 78. In addition, the pick indicator logic 326 may receive input data from the operator via pick buttons 80 associated with each pick module 70, where a particular pick button 80 of a particular pick module 70 may be actuated by the operator 10 to indicate that the operator 10 has completed retrieving products from the aligned storage bin 72 corresponding to the particular pick module 70. The processor 300 may receive such data input via a pick button 80 and update batch data for an active batch accordingly.

In these embodiments, the processor 300 may interface with the carousel drive controller 320 to cause the carousel drive controller 320 to operate a motor 102 associated with the ALV carousel unit 32 to rotate the storage carousel 62 an amount determined by the processor 300 based on the location of specific storage bins 72 storing products needed to fill an active order. Furthermore, following aligning a vertical storage column 98 to the pick location 88 by rotating the storage carousel 62, the processor 300 may interface with the pick indicator logic 326 to thereby selectively operate one or more pick modules 70, associated with storage bins 72 storing products needed to fill the customer order, to thereby selectively identify storage bins 72 from which the operator should retrieve products.

The carousel drive controller 320 may be connected to position indexing logic 100 configured to monitor which vertical storage column 98 is aligned to the pick location 88 and communicate such positional data to the processor 300. As such in these embodiments, the processor 300 may analyze the positional data received from the carousel drive controller 320 to determine a direction of rotation and degree of rotation in which the storage carousel 62 should be rotated to align particular storage bins 72 storing products required to fill a customer order. The processor 300 may interface with the carousel drive controller 320 based on such determined direction and degree of rotation to rotate the storage carousel 62 such that the operator may retrieve products needed to fill a customer order.

More specifically, the carousel drive controller 320 may be operated according to logic that causes the vertical storage columns 98 to be presented in an efficient and streamlined manner to the opening 88. To this end, the vertical storage column 98 with the highest number of medical items to be picked is positioned at the opening 88 first. The multiple medical items may all be contained in one storage bin 72 or spread across multiple storage bins 72. After all of the picks are completed in that vertical storage column 98, the next vertical storage column 98 to be presented is selected based on which vertical storage column 98 contains the highest number of picks remaining, or the closest of these if multiple vertical storage columns 98 contain the highest number of picks remaining Thus, the movement of the storage carousel 62 is streamlined or minimized.

In some embodiments consistent with the invention, the memory 302 includes a storage database 306 that in turn includes one or more bin records 328. A bin record 328 generally includes data corresponding to a particular storage bin 72, including, for example, data corresponding to the product stored in the particular storage bin 72 such as the medical item name, dosage, quantity per product, expiration date, lot number, controlled substance schedule number, the quantity of units of the product stored in the location, and/or other such relevant information. As such, embodiments of the invention may include a bin record 328 corresponding to each storage bin 72 of each carousel storage unit 32. The memory 302 may also store an active order data structure 308 including batch data 330, where the batch data 330 may indicate each unit of product required to be picked and a patient associated with each unit (referred to herein as a pick) of an active batch of pick; in addition, the batch data 330 may store data indicating a particular customer (e.g., customer facility, customer pharmacy, etc.) and/or other such relevant information needed to pick, label, and verify each pick of the customer order in the active batch. It will be understood that the bin records 328 and the use of the storage bins 72 may be organized in various manners, including separating controlled substances of different schedule levels in different pie-piece-shaped zones within the storage carousel 62. In this regard, different vertical storage columns 98 may include different schedule levels of controller substances.

As shown in FIG. 15, the ALV carousel unit 32 may be in communication with a pharmacy host server 56 over the communication network 313. The pharmacy host server 56 includes at least one processor 342 and a memory 344. In addition, the pharmacy host server 56 includes an I/O interface 346 configured to input data to the processor 342 and output data from the processor 342, to and from one or more connected peripheral devices. The pharmacy host server 56 communicates with the carousel storage unit 32 over the communication network 313 via a network interface controller (TX/RX) 348. The memory 344 includes an application 350 stored therein, where the application includes one or more instructions stored in a format that may be executed by the processor 342 to perform or cause to be performed one or more operations consistent with embodiments of the invention.

Furthermore, the memory 344 may store one or more data structures, including an order database 352, a tote database 354, a product database 356, and/or an operator database 357. The order database 352 may include one or more order records 358, where each order record 358 may correspond to a customer order. An order record 358 may include an identifier corresponding to the customer (e.g., a customer number, customer name, etc.), each product and a corresponding quantity for the customer order (i.e., picks), a patient associated with each unit of each product in the customer order, identification numbers for totes 50 associated with the customer order/batches of the customer order, shipping information associated with the customer order, and/or other such information. The tote database 354 includes one or more tote records 360, where each tote record 360 corresponds to a box/shipping container 50 (i.e., a "tote") utilized in filling customer orders. Each tote record 360 includes data indicating a customer order with which the corresponding tote 56 is associated, batch data corresponding to the tote 50 for the associated customer order, one or more ALV carousel units 32 where products may be retrieved for the tote 50 customer order, a tote type (e.g., a temporary storage tote, a shipping tote, a local delivery tote, etc.), and/or other such information.

The product database 356 includes one or more product records 362, where a product record 362 may store data corresponding to a particular type of product that may be included in a customer order, including products stored in storage bins 72 of ALV carousel units 32 in communication with the pharmacy host server 56 as well as other remote storage locations such as pick-to-light racks 42. A product record 362 may include data corresponding to a type of product, including, for example, a name of the type of product and/or medical item included in the product, dosage of the type of product, quantity of medical items in the product, a U.S. Drug Enforcement Agency (DEA) controlled substance schedule classification associated with the product, any contra-indications with other types of product(s), storage location data indicating any storage bins 72 storing the particular type of product in ALV carousel units 32 and/or remote storage locations storing the type of product, and/or any other information that may be useful in filling customer orders.

The operator database 357 includes one or more operator records 366, where each operator record 366 corresponds to the operator that may pick products for customer orders consistent with embodiments of the invention. Each operator record 366 may include data corresponding to the operator, such as an identifier associated with the operator (e.g., the operator's name, an employee identification number, etc.), login credentials associated with the operator including an identification credential (e.g., a user name, identification number, etc.) and an identity verification credential (e.g., a password, a pin number, a key fob number, a biometric registration, etc.), a DEA drug class permission, and/or other such information.

While the data structures 306, 308, 352, 354, 356, 357 are illustrated in FIG. 15 as individual data structures resident on the memory 344 of the pharmacy host server 56 or the memory 302 of the ALV carousel unit 32, the invention is not so limited. For example, the data represented by the data structures 306, 308, 352, 354, 356, 357 may be combined in one or more data structures, such as one or more relational databases. Moreover, the memory 302, 344 may generally be considered local and/or remote memories accessible by the processors 300, 342 over a local bus network and/or a communication network such as network 313 illustrated in FIG. 15. The memory 302, 344 may represent random access memory (RAM) comprising the main storage of a computer, as well as supplemental levels of memory, e.g., cache memories, non-volatile or backup memories (e.g., programmable or flash memories), mass storage memory, read-only memories (ROM), etc. In addition, the memory 302, 344 may be considered to include memory storage physically located elsewhere, e.g., cache memory in a processor of any computing system in communication with the ALV carousel unit 32 and/or pharmacy host server 56, as well as any storage device on any computing system in communication with the ALV carousel unit 32 and/or pharmacy host server 56 (e.g., a remote storage database, a memory device of a remote computing device, cloud storage, etc.).

Figure 16:
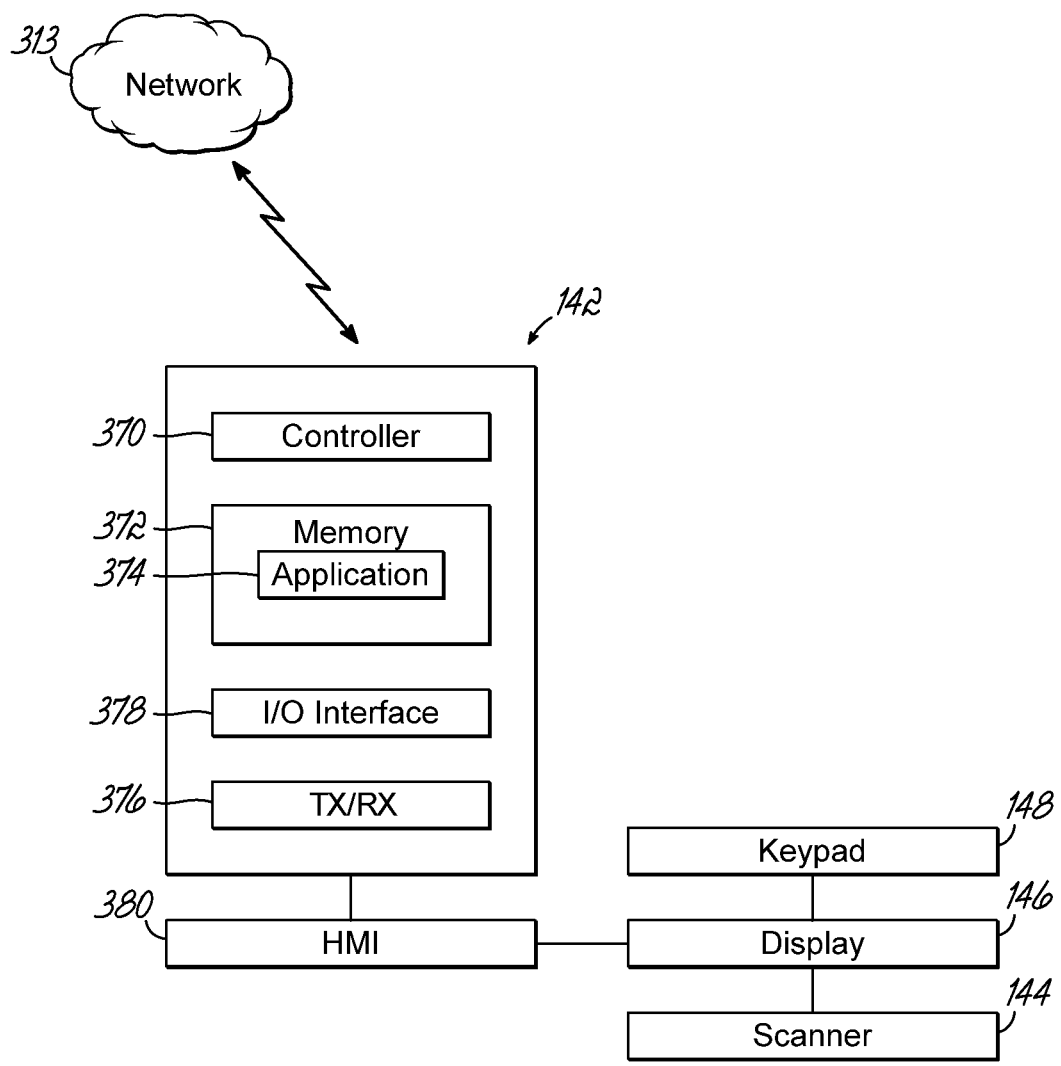
FIG. 16 is a block diagram illustrating components of the hand scanner of FIG. 9.

Turning now to FIG. 16, this figure provides a block diagram illustrating components of a manual or hand scanner 142 consistent with some embodiments of the invention. As shown, the hand scanner 142 includes a controller 370 (e.g., a general/special purpose processor/microcontroller) a memory 372, and an application 374 stored in the memory 372. As discussed previously, the application 374 generally includes program code comprising one or more instructions stored in a format executable by the controller 370 to perform one or more operations consistent with embodiments of the invention. In particular, the application 374 of the hand scanner 142 includes instructions directed to scanning and processing readable indicia (e.g., a barcode, a QR code, and RFID chip, etc.) of products, totes 50, and/or storage locations (including storage bins 72 of one or more ALV carousel units 32 and storage locations 140 on the pick-to-light racks 42); providing information related to such scanned products, totes 50, and/or storage locations; providing instructions to the operator utilizing the hand scanner 142 to facilitate refilling and/or picking products; and communicating with the pharmacy host server 56 to facilitate refilling and/or picking products.

The hand scanner 142 includes a transceiver ("Tx/Rx") 376 may be utilized by the controller 370 to communicate data with a pharmacy host server 56 and/or one or more ALV carousel units 32 over the communication network 313. As illustrated previously in FIG. 9A, the hand scanner 142 includes a keypad 148 for interfacing with the operator to receive input data, a display screen 146 for outputting data to the operator in an understandable format, and a scanner 144 (e.g., a barcode scanner, QR code scanner, RFID reader, and/or other such input peripherals) for scanning machine readable indicia. The hand scanner 142 includes an I/O interface 378 for communicating data between the controller 370 and one or more peripherals, such as an HMI 380 and/or the scanner 144. The HMI 380 generally comprises a machine interface which receives input data from the operator via one or more input peripherals (e.g., the keypad 148, a microphone, a touch-screen, etc.) and outputs data to one or more output peripherals (e.g., the display 146, speakers, light indicators, etc.).

In general, the hand scanner 142, pharmacy host server 56, and one or more ALV carousel units 32 may be in communication over the communication network 313. As such, in response to receiving data at the hand scanner 142, pharmacy host server 56, and/or ALV carousel unit(s) 32, such data may be communicated over the communication network 313 to the other devices 142, 56, 32 substantially in real time. With respect to the flowcharts described herein, in some cases, communications between the hand scanner 142, pharmacy host server 56 and/or ALV carousel unit(s) 32 may not be explicitly provided. However, such communications are contemplated in embodiments of the invention unless explicitly stated otherwise.

Figure 17:
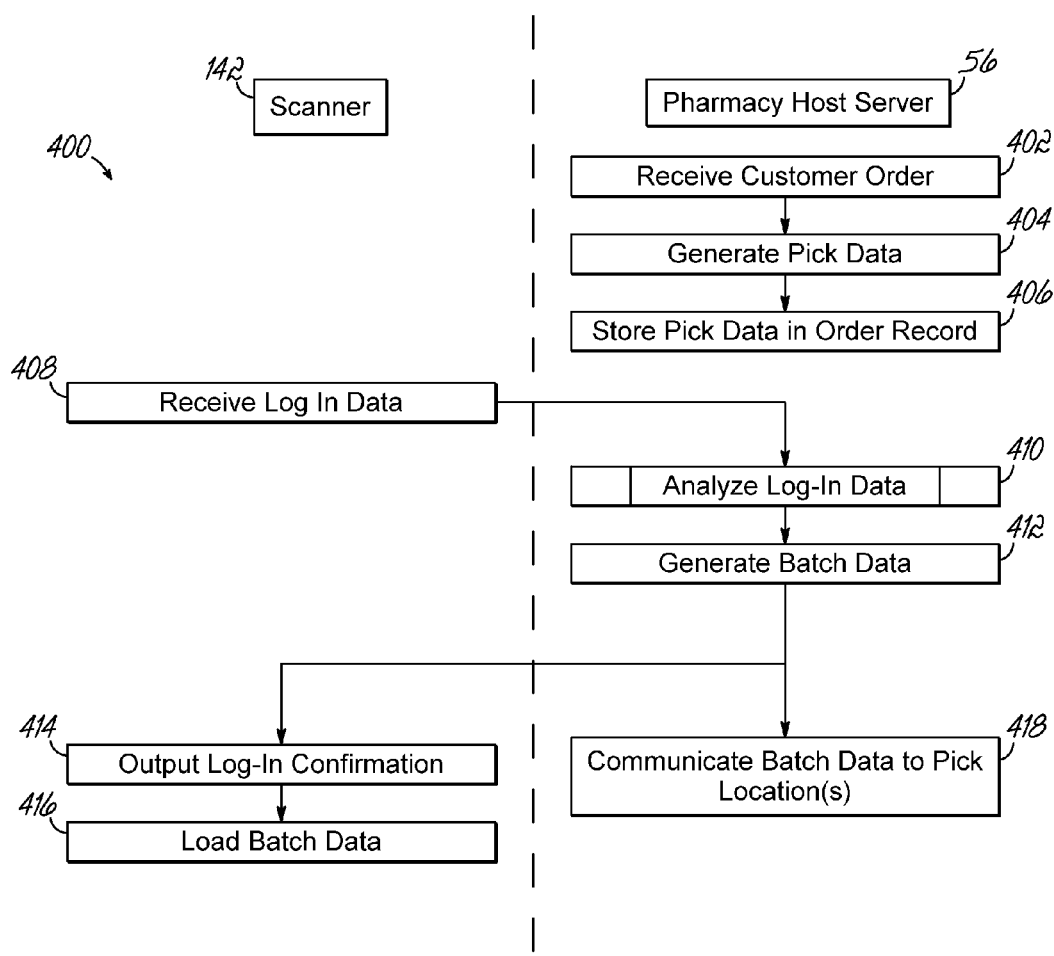
FIG. 17 is a block diagram showing a sequence of operations that may be performed during initial start up and order retrieval of the ALV system of FIG. 2.

Turning now to FIG. 17, this figure provides flowchart 400 which illustrates a sequence of operations that may be performed by a hand scanner 142 and pharmacy host server 56 consistent with embodiments of the invention. The pharmacy host server 56 receives a customer order including a plurality of picks required to be labeled and verified (block 402). The pharmacy host server 56 generates pick data based on the customer order (block 404), where the pick data indicates each product required for the customer order, the quantity of units for each product, and a patient associated with each unit of each product. The pharmacy host server 56 stores the pick data in at least one order record 358 of the order database 352 (block 406). In general, each order record 358 may include a table data structure that stores the pending picks.

An operator may log-in to retrieve picks from remote storage locations 72, 140, including one or more ALV carousel units 32 using the hand scanner 142. The hand scanner 142 receives the log-in data (block 408) and communicates the log-in data to the pharmacy host server 56 for processing (block 410). After verifying the operator's log-in, the pharmacy host server generates batch data for the operator based on the pick data stored in the order record 358 (block 412). The pharmacy host server 56 communicates a log-in confirmation and batch data to the hand scanner 142. The hand scanner 142 outputs the data to the associated display 146 indicating that the operator's log-in data is valid (block 414), and the hand scanner 142 loads the batch data (block 416). In some embodiments, loading the batch data may include outputting each pick and a storage location at which the pick may be retrieved in list format to the display 146. In addition, in some embodiments, the pharmacy host server 56 may communicate the batch data to one or more pick locations having pick-to-light indication systems such as the pick modules 70, including, for example, one or more ALV carousel units 32 that store products of the batch data (block 418).

Further logic may be used to ascertain that additional medical items for a particular customer order are in process under pharmacist order review and not released to the pharmacy floor for processing yet (e.g., a portion of the medical items are ready to be filled and labeled, while another portion of the same order is still under review and will be added to the order queue shortly). If this condition is present, particular batches of customer orders may be flagged or held in a suspended state until remaining elements of and/or medication orders are complete with their clinical verification by a pharmacist and released for order fulfillment. This temporary suppression of the customer orders associated with this condition remove fragmenting of orders that can increase the inefficiencies in the filling process.

Figure 18:
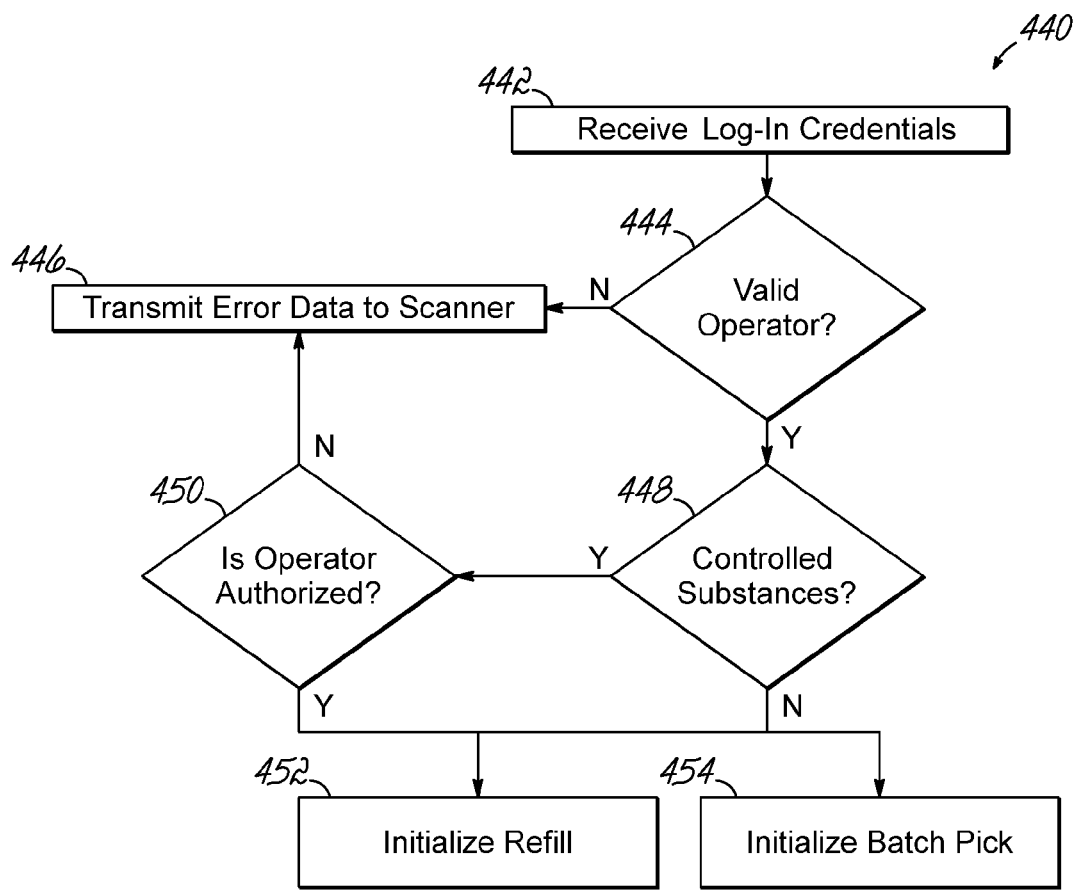
FIG. 18 is a block diagram showing a sequence of operations that may be performed during an operator log in process used with the ALV system of FIG. 2.

FIG. 18 provides flowchart 440 that illustrates a sequence of operations that may be performed by a pharmacy host server 56 consistent with embodiments of the invention to analyze log-in data received from a hand scanner 142 for verification. The pharmacy host server 56 may receive log-in credentials (block 442) at associated processor 342 communicated from the hand scanner 142. In some embodiments, the operator may type in a user name and password via keypad 148. In some embodiments, the operator may scan a security device using scanner 144 associated with the hand scanner 142 (i.e., a badge, ID card, key fob, biometric registration, etc.), and the operator may type in a pin number. Other such known methods for identification verification may be utilized.

The processor 342 of the pharmacy host server 56 determines whether the log-in credentials match a valid operator (block 444). In these embodiments, the processor 342 may access/query the operator database 357 to determine whether the log-in credentials match a valid operator. In response to determining that the log-in credentials do not match a valid operator ("N" branch of block 444), the processor 342 communicates error data to the hand scanner 142 such that the display 146 of the hand scanner 142 may indicate to the operator that the log-in credentials are not valid (block 446), and the hand scanner 142 may request that the operator re-enter the log-in credentials. In response to determining that the log-in credentials match a valid operator ("Y" branch of block 444), the processor 342 determines whether an operation which the operator is attempting to perform with the hand scanner 142 includes one or more controlled substances (block 448).

In response to determining that the operation that the operator is attempting to perform with the hand scanner includes controlled substances ("Y" branch of block 448), the processor 342 determines whether the operator is authorized to perform operations including one or more desired classes of controlled substances (block 450). In some embodiments of the invention, the processor 342 may access/query the operator database 357 to determine a controlled substances authorization level, where the level may indicate if the operator is authorized to perform operations with one or more classes of controlled substances. For example, the operator may be authorized to perform operations with class III-V controlled substances but not class II controlled substances. In this example, if the operator were attempting to refill a class II controlled substance using the hand scanner 142, the processor 342 would determine that the operator is not authorized. Furthermore, in some embodiments of the invention, a LV carousel unit 32 associated with the pharmacy host server 56 may store products including different classes of controlled substances, and the processor 342 may communicate data to the LV carousel unit 32 such that the operator is not allowed to access storage bins 72 storing particular classes of controlled substances that the operator is not authorized to access. In some embodiments of the invention, controlling access to such storage bins 72 may include automatically closing a motorized security door 74 associated with a cage 60 to thereby close a pick location 88. In some embodiments, controlling access may include generating pick instructions that do not allow the LV carousel unit 32 to align a vertical storage column 98 that includes one or more storage bins 72 storing controlled substances that the operator is not authorized to access to the pick location 88.

In response to determining that the operator is not authorized to perform the desired operation for one or more desired classes of controlled substances ("N" branch of block 450), the processor 342 communicates error data to the hand scanner 142 such that the display 146 may indicate to the operator that the desired operation is not authorized (block 446), and the hand scanner 142 may return to a log-in screen. In response to determining that the operator is authorized to perform the desired operation for the one or more desired controlled substances ("Y" branch of block 450), or in response to determining that the desired operation does not include any controlled substances ("N" branch of block 448), the pharmacy host server 56 may initialize the desired operation, including, for example, a refill operation (block 452) or a picking operation (block 454).

Figure 19:
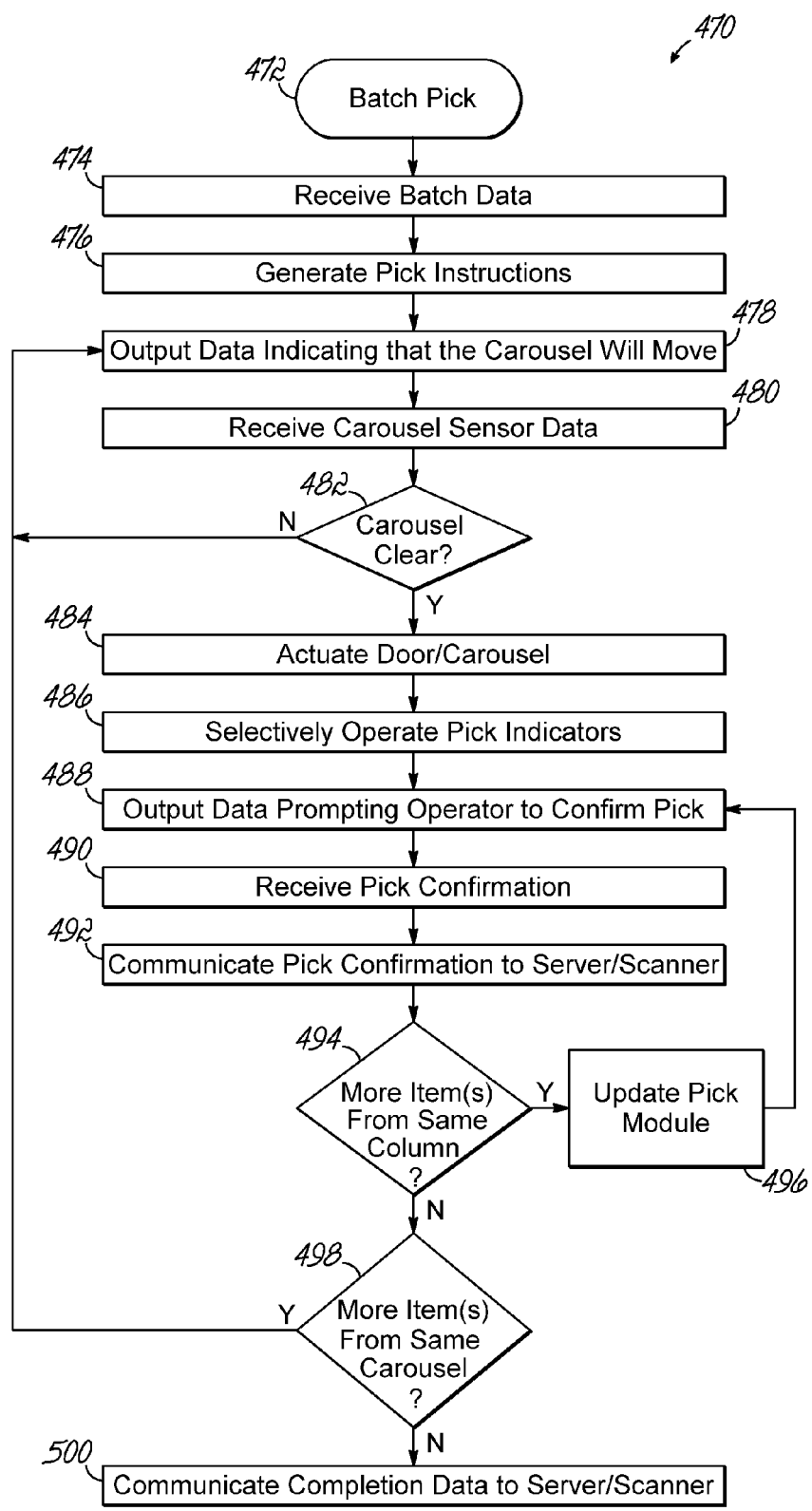
FIG. 19 is a block diagram showing a sequence of operations that may be performed during a batch picking process used with the ALV system of FIG. 2.

Referring to FIG. 19, this figure provides flowchart 470 that provides a sequence of operations that may be performed by ALV carousel unit 32 consistent with embodiments of the invention to facilitate picking of products stored therein. The pharmacy host server 56 may initialize a batch pick operation (block 472). In response to the initialization, a processor associated with the ALV carousel unit 32 receives batch data for the active order (block 474). In response to receiving the batch data, the processor 300 generates pick instructions for the ALV carousel unit (block 476). The pick instructions generally correspond to the interface between the processor 300 and carousel drive controller 320 and the interface between the processor 300 and pick indicator logic 326. In some embodiments of the invention, the pick instructions may cause the processor 300 to interface with the drive controller 320 to thereby cause the drive controller 320 to operate motor 102 connected to the storage carousel 62 of the ALV carousel unit 32 to thereby rotate the storage carousel 62 such that products included in picks of the batch data are positioned in pick location 88. Furthermore, the pick instructions may cause the processor 300 to interface with the pick indicator logic 326 to cause the pick indicator logic to selectively operate pick modules 70, to indicate specific storage bins 72 from which the operator is supposed to retrieve products for the active order. For example, in some embodiments, the pick instructions may preclude aligning particular storage bins 72 to the pick location 88 based on the operator's permission level associated with controlled substances such that controlled substances of one or more classes may not be accessible by the operator. In addition, generating the pick instructions may be based on a stock management policy, including, for example, a First-In-First-Out (FIFO) policy. In such embodiments, if a product is stored in more than one storage bin 72, the storage bin 72 storing units of the product having the earliest expiration date will be utilized to fill a batch to thereby reduce stock loss due to expiration. In addition, the pick instructions may direct the rotation of the storage carousel 62 according to a predefined policy (e.g., the least number of rotations, minimization of rotation time to each vertical column of storage bins 98, and/or other such predefined operation policies).

The processor 300 outputs data indicating that rotation of the storage carousel 62 is imminent (block 478). In some embodiments the processor 300 may output an audible warning via an associated speaker, and/or the processor may output a visual warning via the associated HMI panel 132. In some embodiments, the ALV carousel unit 32 may communicate data to hand scanner 142 being used by the operator, such that the operator may receive the visual and/or audible warning from an output peripheral associated with the hand scanner 142. The processor 300 receives sensor data from one or more sensors associated with the storage carousel 62 (block 480), and the sensor data may be analyzed by the processor 300 to determine whether the pick location 88 is clear (i.e., whether the operator and/or another object is clear of the pick location 88) (block 482). In these embodiments, the processor 300 determines whether the pick location 88 is clear to prevent injury to the operator and/or damage to other objects when rotating the storage carousel 62. In response to determining that the pick location 88 is not clear ("N" branch of block 482), the processor 300 continues outputting a warning (block 478) and receiving sensor data (block 480). In response to determining that the pick location 88 is clear ("Y" branch of block 482), the processor 300 interfaces with the drive controller 320 to cause the storage carousel 62 to rotate and thereby align a vertical storage column 98 to the pick location 88 and to optionally also operate the door 74 (i.e., close the door 74 before rotating the storage carousel 62 and open the door 74 after rotation is complete) (block 484), where at least one storage bin 72 of the vertical storage column 98 aligned to the pick location 88 stores a product included in the customer order/batch data.

The processor 300 interfaces with the pick indicator logic 326 to selectively operate one or more pick modules 70 corresponding to one or more storage bins 72 storing products in the order/batch data (block 486). In these embodiments, the processor may selectively operate particular pick modules 70 by illuminating a light associated with the pick module 70 and/or outputting a quantity for a particular pick to a display 78 associated with the pick module 70. The processor 300 outputs data via the associated HMI panel 132 and/or by communicating data to the hand scanner 142 prompting the operator to confirm each pick after the operator retrieves each unit of a needed product from the aligned storage bin 72 (block 488). The processor 300 receives pick confirmation for each pick (block 490). In some embodiments, the processor 300 may receive pick confirmation via a pick button 80 of the corresponding selectively operated pick module 70. In some embodiments, the processor 300 may receive pick confirmation from the hand scanner 142, where the operator may scan a retrieved product with the hand scanner 142 to confirm the pick. In response to receiving the pick confirmation, the processor 300 may communicate the pick confirmation to the pharmacy host server 56 and/or hand scanner 142 such that the batch data and/or order data are updated (block 492).

Following the confirmation (when applicable), the processor 300 determines whether more units of one or more products in the batch data are stored in the aligned vertical storage column 98 (block 494). In response to determining that one or more items (i.e., one or more units of one or more products) stored in the aligned vertical storage column 98 still need to be picked for the batch ("Y" branch of block 494), the processor updates the pick module 70 based on the confirmation and/or updated batch data (block 496). For example, if the first item from a first storage bin 72 was picked and the batch data updated, and no more items were required from the first storage bin 72, the pick module 70 associated with the first storage bin 72 may be extinguished (i.e., turned off). However, if more items were required from the first storage location, the pick module 70 and/or associated display 78 corresponding to the first storage bin 72 may be updated to reflect the remaining quantity of units in the batch data needed from the first storage bin 72. After updating the pick module 70, the ALV carousel unit 32 performs the operations described above with respect to blocks 488 through 494, until all items stored in the aligned vertical storage column 98 have been picked ("N" branch of block 494). The processor 300 determines whether any more items in the batch data are stored in the storage carousel (block 498).

In response to determining that one or more items of the batch data are stored by the storage carousel 62 ("Y" branch of block 498), the processor 300 actuates the storage carousel 62 to align another vertical storage column 98 including storage bins 72 storing at least one needed item (block 484). The processor 300 and ALV carousel unit 32 perform the operations described in blocks 478 through 498 until all items of the batch data stored by the storage carousel 62 have been picked ("N" branch of block 498). Once all items from the storage carousel 62 in the batch data have been picked ("N" branch of block 498), the processor 300 communicates completion data to the pharmacy host server 56 and/or the hand scanner 142 (block 500).

In some embodiments, in response to determining that one or more items in the batch data have not been picked the pharmacy host server 56 may determine remote storage locations at which the unpicked items in the batch data may be located, and the pharmacy host server 56 may communicate data to the hand scanner 142 such that the display 146 informs the operator of such remote locations. For example, one or more unprocessed items in the batch data may be located at second ALV carousel unit 32, and the pharmacy host server 56 may access product database 356 and/or storage database 306 to identify the second ALV carousel unit 32, and the pharmacy host server may communicate data to the hand scanner 142 such that the display 146 identifies the second ALV carousel unit 32. As another example, one or more items may be located in a remote shelf, and the operator may be provided information that identifies the remote shelf (such as, for example, by illumination of further pick modules 70 adjacent the locations 72, 140).

Figure 20:
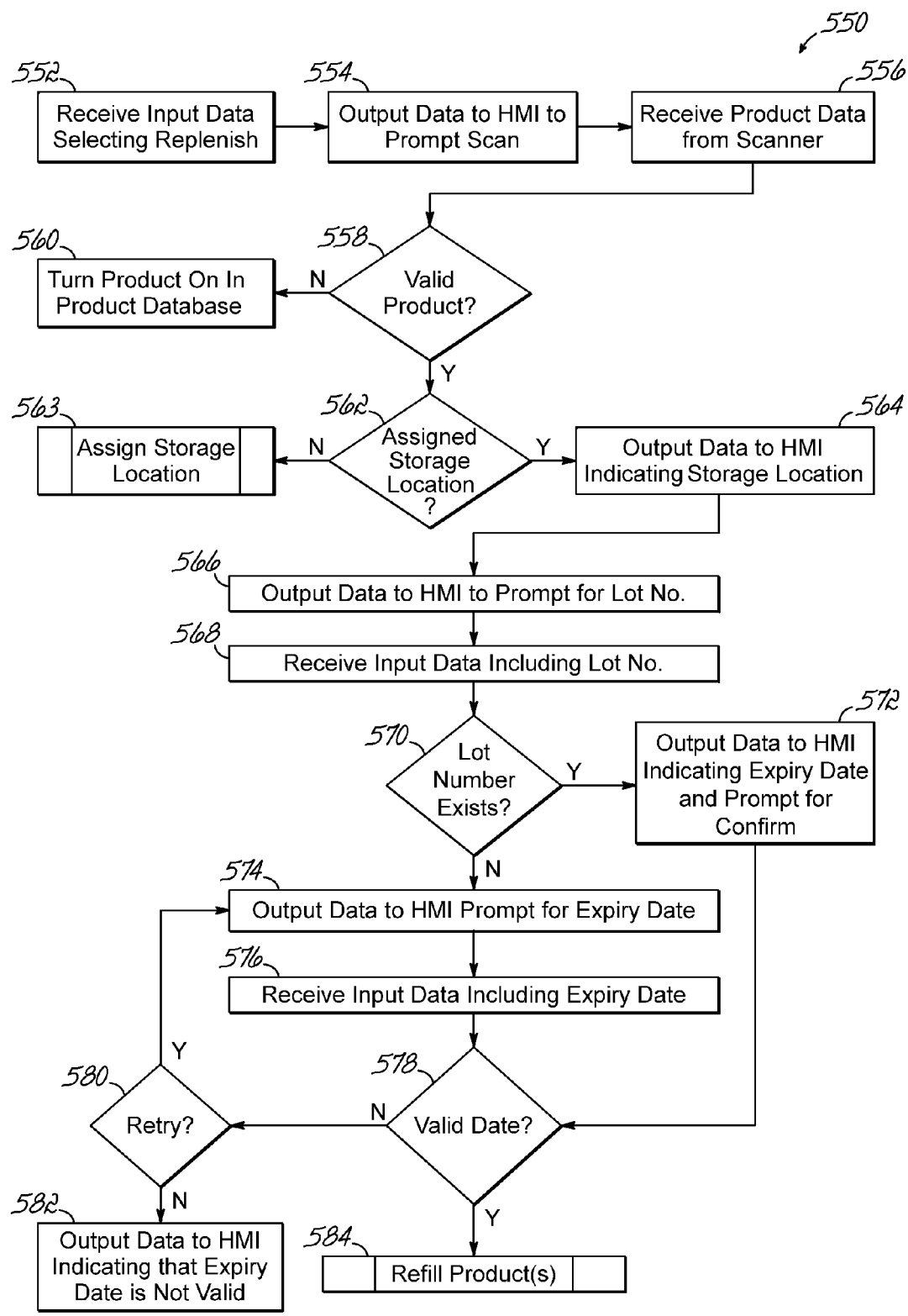
FIG. 20 is a block diagram showing a sequence of operations that may be performed during a replenishment process used with the ALV system of FIG. 2.

FIG. 20 provides flowchart 550 which illustrates a sequence of operations that may be performed by a hand scanner 142, pharmacy host server 56 and/or ALV carousel unit 32 consistent with embodiments of the invention to perform replenishment and refill operations for a storage carousel 62 associated with the ALV carousel unit 32. The operator may input data to the hand scanner 142 indicating that the operator is going to replenish a product (block 552). A controller 370 of the hand scanner 142 outputs data to HMI 380 associated with the hand scanner 142 such that a display 146 associated with the HMI 380 prompts the operator to scan a product (block 554). The operator may scan a product using scanner 144 of the hand scanner 142, and the controller 370 may receive product data from the scanner 144 (block 556).

Processor 342 of the pharmacy host server 56 analyzes the received product data to determine whether the product is a valid product for the pharmacy host server 56 (i.e., a product that is stocked in a facility utilizing the pharmacy host server 56) (block 558). In some embodiments, the processor 342 may access and/or query a product database 356 stored at the pharmacy host server 56 to determine whether the product is a valid product. In response to determining that the product is not a valid product ("N" branch of block 558), the processor 342 may "turn on" the product in the product database 356 based on the received product data and/or user input data provided at the hand scanner 142 and/or the pharmacy host server (block 560). "Turning on" the product may include generating a product record 362 and storing the product record 362 in the product database 356.

In response to determining that the scanned product is a valid product ("Y" branch of block 558), the processor 342 determines whether the product is assigned to a storage location, such as a storage bin 72 of the ALV carousel unit 32 (block 562). In such embodiments, the processor 342 may analyze storage database 306 and/or product database 356 to determine whether the product is assigned to a storage location. In response to determining that the product is not assigned to a storage location ("N" branch of block 562), the processor 342 may initialize a storage location assignment operation (block 563). In response to determining that the product is assigned to a storage location ("Y" branch of block 562), the controller 370 of the hand-held scanner 142 outputs data to the HMI 380 such that the associated display 146 indicates a remote storage location at which the product may be stocked (block 564). In response to determining that the scanned product is assigned to a storage location, the controller 370 outputs data to the HMI 380 such that the display 146 prompts the operator to input a lot number associated with the scanned product (block 566). The operator may input a lot number via the keypad 148, and the processor of the pharmacy host server 342 receives the input lot number (block 568) and then determines whether the lot number of the product has been previously input in to the pharmacy host server (block 570).

In response to determining that the lot number exists ("Y" branch of block 570), the controller 370 of the hand scanner 142 outputs data to the HMI 380 and the display 146 indicates an expiry date associated with the existing lot number and prompts the operator to confirm the expiry date (block 572). In response to determining that the lot number of the product does not exist ("N" branch of block 570), the controller 370 outputs data to the HMI 380 and the display 146 prompts the operator to input an expiry date associated with the scanned product and lot number (block 574). The operator may input an expiry date associated with the product via the keypad 148, and the controller 370 of the hand scanner 142 receives the input data including the expiry date. The input data may be communicated from the hand scanner 142 to the processor 342 of the pharmacy host server 56 over the communication network 313 (block 576). Following input or confirmation of the expiry date, the processor 342 determines whether the expiry date is a valid date (block 578). In embodiments of the invention, products may not be stocked in a storage location if the expiry date is within a fixed time from the date that the replenishment is occurring. For example, in some embodiments, the expiry date may be determined to be invalid if the expiry date falls within a fixed time of 45 days, for example, from the date on which the operator is attempting to stock the associated product. In this manner, the pharmacy host server 56 and/or hand scanner 142 may control inventory and expiry dates to prevent significant stock loss due to expiry of the products.

In response to determining that the expiry date is not valid ("N" branch of block 578), the processor 342 may determine whether to retry the input and evaluation of the expiry date (block 580), and in response to determining to retry the input and evaluation the pharmacy host server 56 and/or hand scanner 142 may repeat the operations described in blocks 574 through 578. After retrying the input and evaluation of the expiry date a predetermined number of times ("N" branch of block 580), the controller 370 of the hand scanner 142 outputs data to the HMI 380 such that the display 146 indicates to the operator that the expiry date is not valid and the product cannot be stocked (block 582). In response to determining that the expiry date is valid ("Y" branch of block 578), the pharmacy host server 56, hand scanner 142 and/or the ALV carousel unit 32 may perform operations associated with refilling the product as described in FIG. 21 (block 584).

Figure 21:
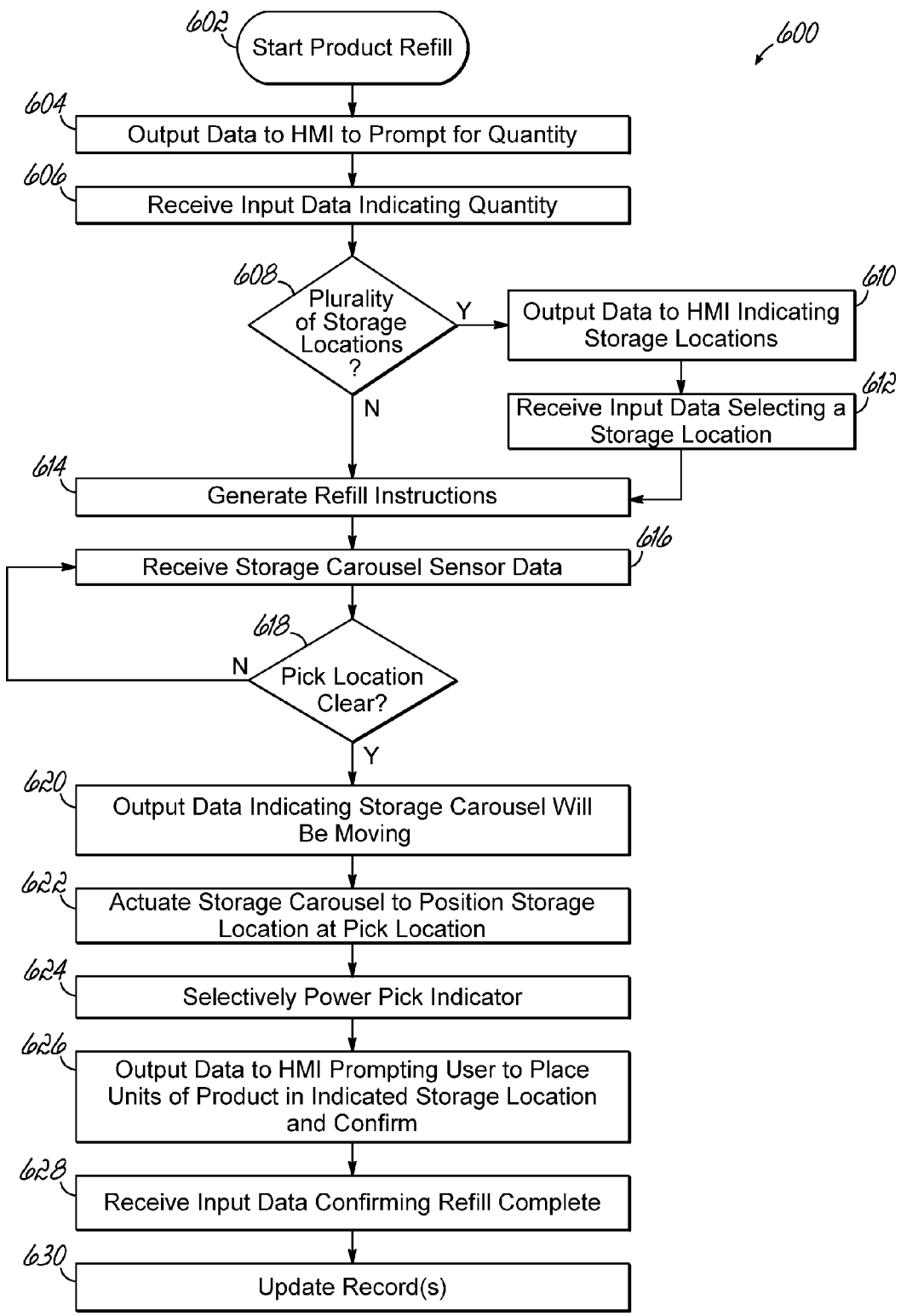
FIG. 21 is a block diagram showing a further sequence of operations that may be performed during the replenishment process of FIG. 20.

FIG. 21 provides a flowchart 600 that illustrates a sequence of operations that may be performed by pharmacy host server 56, hand scanner 142 and/or ALV carousel unit 32 consistent with embodiments of the invention to facilitate the operator refilling a product after providing information associated with the product as described in flowchart 550 of FIG. 20. A product refill is initialized at the ALV carousel unit 32 with the hand scanner 142 (block 602). A controller 370 associated with the hand scanner 142 outputs data to the HMI 380 associated with the hand scanner 142 such that display 146 in communication with the HMI 380 prompts the operator to input a quantity of units of the product to be refilled (block 604). The operator may input a quantity of units of the product to be refilled in the ALV carousel unit 32, and the pharmacy host server 56 may receive the input data indicating such quantity (block 606). A processor 342 of the pharmacy host server 56 determines whether the product is assigned more than one storage bins 72 on the storage carousel 62 associated with the ALV carousel unit 32 (block 608). In some embodiments, the processor 342 may access and/or query a product database 356 and/or a storage database 306 to determine whether the product is assigned to a plurality of storage bins 72 of the ALV carousel unit 32.

In response to determining that the product is stored in a plurality of storage bins 72 ("Y" branch of block 608), the controller 370 of the hand scanner 142 outputs data to the HMI 380 such that the display 146 informs the operator of the plurality of storage bins 72 (block 610). The operator may select a particular storage bin 72 via the keypad 148 and/or the operator may scan machine readable indicia 116 associated with a particular storage bin 72, and the controller 370 may receive input data indicating the selected storage bin 72 (block 612), which may be forwarded to the pharmacy host server 56 and/or ALV carousel unit 32. Based on the selected storage bin 72, the processor 300 of the ALV carousel unit and/or the processor 342 of the pharmacy host server 56 generate refill instructions (block 614). The refill instructions generally correspond to an interface between the processor 300 of the ALV carousel unit and a drive controller 320 connected between a motor 102 of the storage carousel 62 and the processor 300, and the refill instructions further generally correspond to an interface between the processor 300 and pick indicator logic 326 connected between pick modules 70 and the processor 300. According to the pick instructions, the processor 300 interfaces with the drive controller 320 and the pick indicator logic 326 to rotate the storage carousel 108 to align a vertical storage column 98 including the selected storage bin 72 to the pick location 88 accessible by the operator and to selectively operate a particular pick module 70 to indicate the selected storage bin 72 for the operator.

The processor 300 receives sensor data from one or more sensors 90 associated with the ALV carousel unit 32 (block 616), and the sensor data may be analyzed by the processor 300 to determine whether the pick location 88 is unobstructed or clear (i.e., whether the operator and/or another object is clear of the pick location 88) (block 618). In response to determining that the pick location 88 is not clear ("N" branch of block 618), the processor 300 continues receiving sensor data (block 616). In response to determining that the pick location 88 is clear ("Y" branch of block 618), the processor 300 outputs data to the HMI panel 132 associated with the ALV carousel unit 32 such that an associated output peripheral optionally informs the operator that the storage carousel 62 is preparing to rotate (block 620). The processor 300 interfaces with the drive controller 320 to cause the storage carousel 62 to rotate and thereby align a vertical storage column 98 including the selected storage bin 72 to the pick location 88 (block 622). The processor 300 interfaces with the pick indicator logic 326 to selectively operate the pick module 70 corresponding to the selected storage bin 72 (block 624).

The controller 370 of the hand scanner 142 outputs data to the HMI 380 such that the display 146 prompts the operator to place the scanned product in the indicated storage bin 72, and/or the processor 300 outputs data to the HMI panel 132 such that the output peripheral of the ALV carousel unit 32 prompts the operator to place the scanned product in the indicated storage bin 72, and the display 146 or output peripheral may request the operator to confirm when stocking is complete via the HMI 380 (block 626). The operator provides confirmation of completing the stocking of the scanned product (block 628). In some embodiments the operator may confirm restocking by actuating a pick button 80 of the selectively operated pick module 70. In some embodiments, the operator may confirm restocking by scanning machine readable indicia 116 associated with the selected storage bin 72 using the hand scanner 142. The confirmation is received by the processor 342 of the pharmacy host server 56, and the processor 342 updates one or more records (block 630) responsive to receiving the confirmation, including, for example, a product record 362 associated with the scanned product, a bin record 328 associated with the selected storage bin 72, the operator record 366 associated with the operator, and/or other such records.

Figure 22:
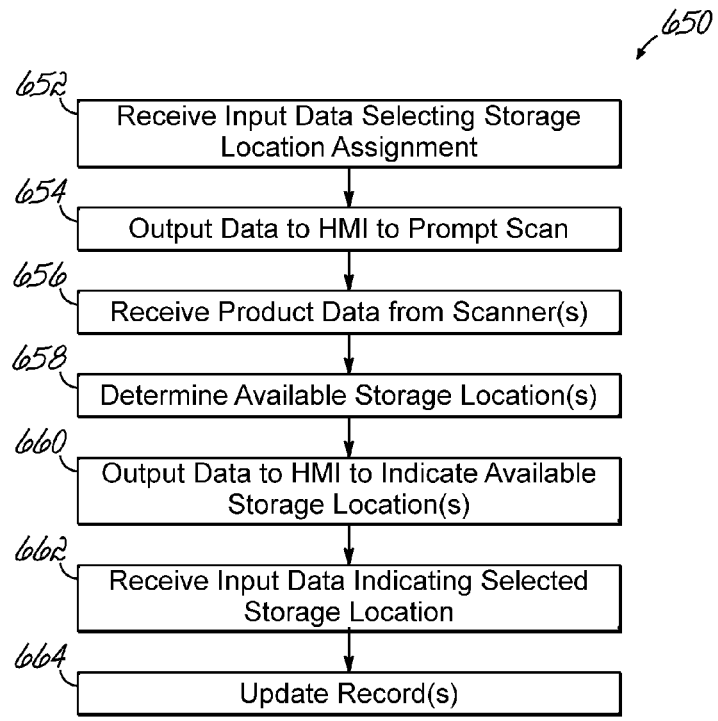
FIG. 22 is a block diagram showing a sequence of operations that may be performed during a storage location assignment process used with the ALV system of FIG. 2.

FIG. 22 provides flowchart 650, where the flowchart 650 illustrates a sequence of operations that may be performed by hand scanner 142 and/or pharmacy host server 56 consistent with some embodiments of the invention to assign a product to a storage location, including, for example, a storage bin 72 of ALV carousel unit 32. The operator may select via keypad 148 and HMI 380 associated with the hand scanner 142 to select a storage bin 72 for assignment, and a controller 370 associated with the hand scanner 142 may receive input data from the HMI 380 selecting to perform a storage location assignment (block 652). In response to receiving input data selecting to perform a storage location assignment, the controller 370 outputs data to the HMI 380 such that display 146 associated with the HMI 380 prompts the operator to scan a product (block 654). The operator may scan the product using barcode scanner 144 of the hand scanner 142. The controller 370 receives product data from the barcode scanner 144 (block 656), which may be communicated to processor 342 of the pharmacy host server 56, and the processor 342 determines available storage bins 72 in the ALV carousel unit 32 (block 658). In these embodiments, the processor 342 may access/query storage database 306 to determine available storage bins 72.

The processor 342 communicates data to the hand scanner 142 indicating the available storage locations, and the HMI 380 outputs the available storage bins 72 on the ALV carousel unit 32 with the display 146 (block 660). The operator may select a particular available storage location 72 with the keypad of the hand scanner 148 and/or by scanning a machine readable indicia (e.g., a barcode) 116 associated with the available storage bin 72, and the controller 370 may receive input data indicating such selection (block 662). The processor of the pharmacy host server 56 may receive selection data from the hand scanner 142, and the processor 300 updates one or more records based on the selected storage location (block 664), including, for example, a product database 356 and/or a storage database 306.

Figure 23:
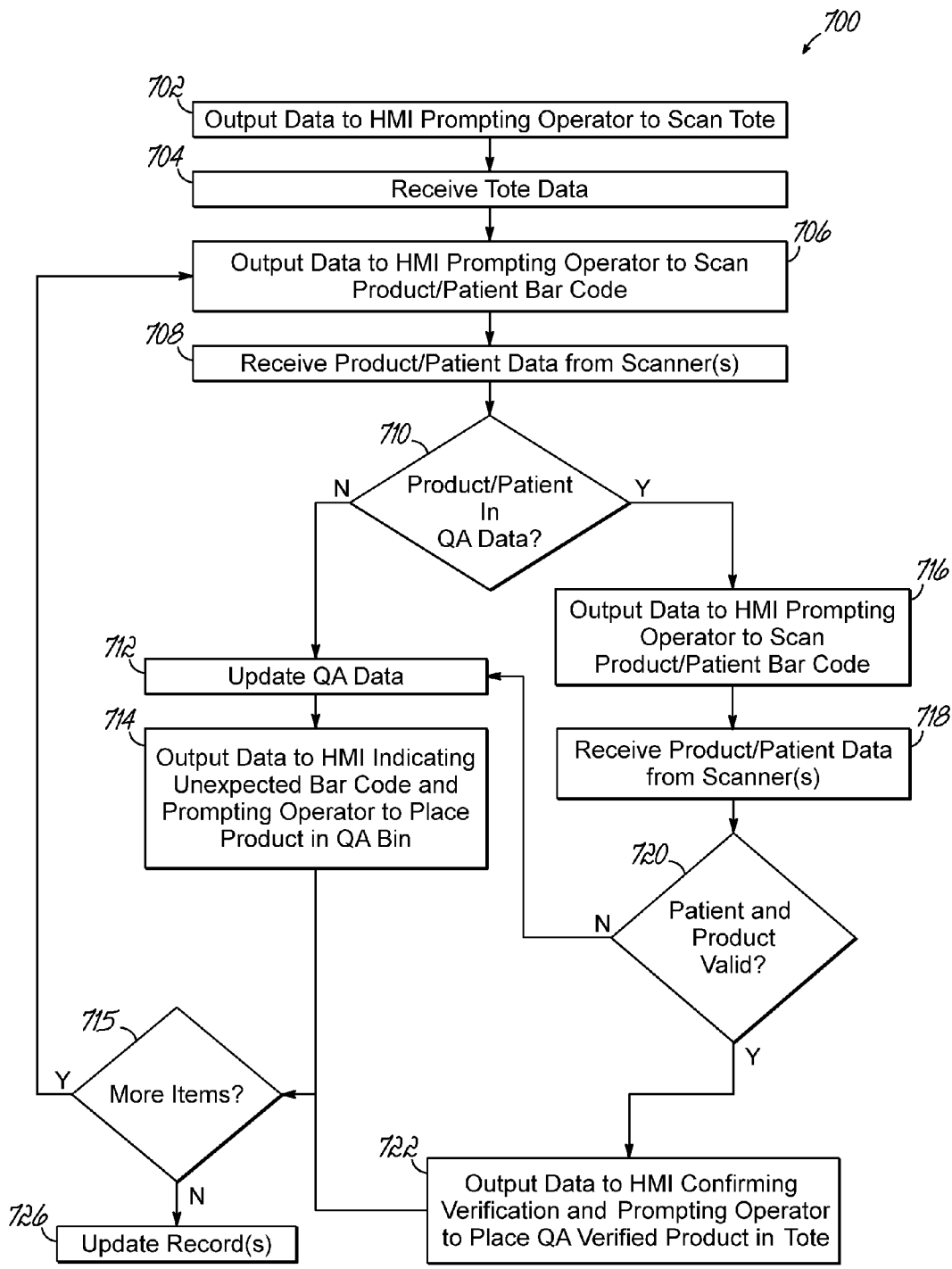
FIG. 23 is a block diagram showing a sequence of operations that may be performed during a tote audit process used with the ALV system of FIG. 2.

With reference to FIG. 23, this figure provides flowchart 700, which illustrates a sequence of operations that may be performed by hand scanner 142 and/or pharmacy host server 56 consistent with embodiments of the invention to perform quality assurance (QA) operations on a tote 50 of labeled and verified items, such as at the audit station 204. A controller 370 associated with the hand scanner 142 may output data to HMI 380 such that the associated display 146 prompts the operator to scan a tote 50 to start a QA process (block 702). An operator may scan a machine readable indicia with scanner 144 associated with the hand scanner 142, and the controller 370 and/or processor 342 of the pharmacy host server 56 may receive tote data (block 704). The controller 370 outputs data to the HMI 380 such that the display 146 prompts the operator to scan product barcode 152 or patient barcode 160 on a first labeled and verified product of the tote 50 (block 706). The operator scans the patient/product barcode 152, 160, and the controller 370 or processor 342 receives data indicating the patient/product (block 708). The processor 342 determines whether the patient/product indicated in the received data is in QA data associated with the tote 50 (block 710). In these embodiments, the processor 342 may access/query tote database 354 corresponding to the scanned tote 50 to determine whether the indicated patient/product is in the QA data, where the QA data includes a list of products that should be labeled with particular patient labels 158 in the tote 50.

In response to determining that the indicated patient/product is not in the QA data ("N" branch of block 710), the processor 342 updates the QA data to indicate that an unexpected patient/product was in the tote 56 (block 712), and the controller 370 of the hand scanner 142 outputs data to the HMI 380 such that the display 146 indicates that the scanned product/patient was unexpected and prompts the operator to place the scanned product in a QA bin (block 714). The processor 342 determines whether more labeled and verified products in the tote 50 need to be QA processed (block 715). If more products need to be QA processed for the tote 50 ("Y" branch of block 715), the hand scanner 142 and/or pharmacy host server 56 may perform the operations described with respect to flowchart 700 for each of the remaining labeled and verified products.

In response to determining that the indicated product/patient is in the QA data ("Y" branch of block 710), the controller 370 outputs data to the HMI 380 such that the display 146 prompts the operator to scan whichever barcode of the product/patient barcode that was not scanned first (i.e., the relevant barcode) (block 716). The operator scans the relevant barcode 152, 160 with the hand scanner 142, and the processor 342 receives data indicating the product/patient from the hand scanner 142 (block 718). The processor 342 determines whether the indicated patient is valid for the indicated product in the QA data (block 720). In response to determining that the patient/product are invalid ("N" branch of block 720), the hand scanner 142 and/or pharmacy host server 56 perform the operations described above with respect to blocks 712 through 714. In response to determining that the indicated patient is valid for the indicated product ("Y" branch of block 720), the controller 370 outputs data to the HMI 380 such that the display 146 indicates that the verification has been confirmed and prompts the operator to place the QA verified product in the tote 50 (block 722). The processor 342 determines whether more labeled and verified products in the tote 50 need to be QA verified (block 715). If more products need to be QA processed for the tote 50 ("Y" branch of block 715), the hand scanner 142 and/or pharmacy host server 56 returns to block 706 and may perform the operations described with respect to flowchart 700 for each of the remaining labeled and verified products. When all products of the tote 50 have been QA verified ("N" branch of block 715), the processor 342 may update one or more records in one or more databases (block 726), including, for example, a particular tote record 360 corresponding to the tote 50 in the tote database 354.

Figure 24:
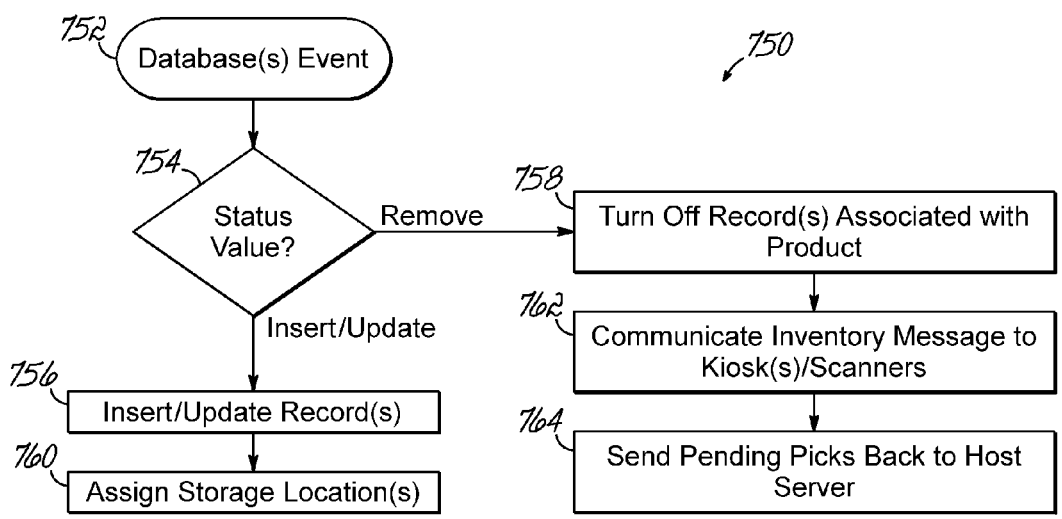
FIG. 24 is a block diagram showing a sequence of operations that may be performed during a database record updating process used with the ALV system of FIG. 2.

FIG. 24 provides flowchart 750, which provides a sequence of operations that may be performed by one or more hand scanners 142, one or more ALV carousel units 32, and/or a pharmacy host server 56 consistent with embodiments of the invention to update records and pick data loaded at one or more ALV carousel units 32 or hand scanners 142. An event may occur in a database of the one or more ALV carousel units 32 and/or pharmacy host server 56 (block 752), including, for example, a product record 362 of a product database 356 may be updated, inserted, or removed. In response to the database event, processor 342 of the pharmacy host server 56 determines a status associated with the database event (block 754).

Based on the determined status, the processor 342 of the pharmacy host server 56 may insert/update one or more records in one or more databases responsive to an insert/update event occurring in a first database (block 756), or the processor 342 of the pharmacy host server 56 may "turn off" one or more records of one or more databases responsive to a remove event occurring in the first database (block 758). In response to the insert/update of one or more records, the processor 342 of the pharmacy host server 56 may assign one or more available storage locations to a product associated with the insert/update (block 760). In response to "turning off" one or more records associated with a particular product, the pharmacy host server 56 may communicate an inventory message to one or more ALV carousel units 32 or hand scanners 142 (block 762), where the inventory message indicates that the "turned off" product may not be picked for a customer order. In response to receiving the inventory message, the one or more ALV carousel units 32 or hand scanners 142 communicate the picks associated with the "turned off" product back to the pharmacy host server 56 such that the picks will not be filled (block 764).

For example, if a recall is issued for a product, the pharmacy host server 56 may communicate an inventory message to all ALV carousel units 32 or hand scanners 142 such that none of the recalled lot number will be put into customer orders. As a further example, if a particular lot number of a product expired, the pharmacy host server 56 may communicate the inventory message to all hand scanners 142 and/or ALV carousel units 32 storing the expired units of product such that the expired units will not be used in filling a customer order. In these embodiments, during generation of the pick instructions, storage bins 72 storing such removed products will not be presented to the operator for retrieval. Hence, in such embodiments, even if the removed product has not yet been physically removed from a storage carousel 62, the removed product will not be used in filling customer orders.

Figure 25:
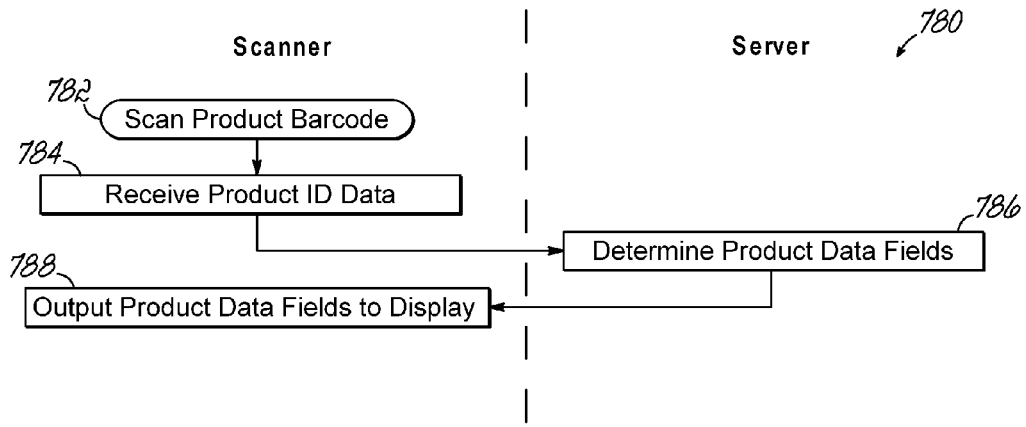
FIG. 25 is a block diagram showing a sequence of operations that may be performed during a product query process used with the ALV system of FIG. 2.
Figure 26:
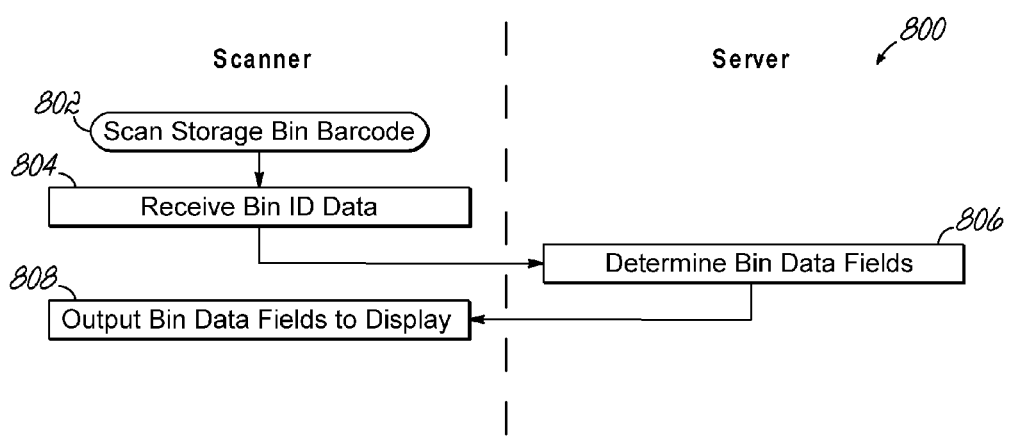
FIG. 26 is a block diagram showing a sequence of operations that may be performed during a storage location query process used with the ALV system of FIG. 2.
Figure 27:
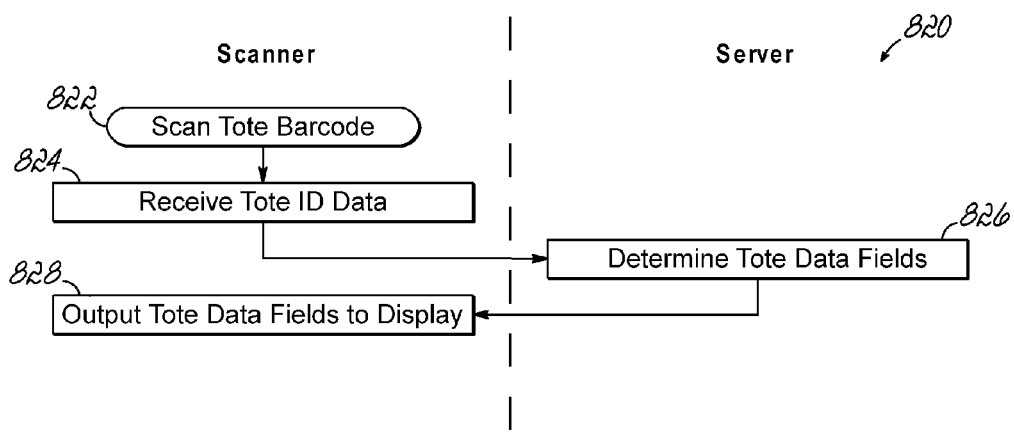
FIG. 27 is a block diagram showing a sequence of operations that may be performed during a tote query process used with the ALV system of FIG. 2.

In some embodiments consistent with the invention, the hand scanner 142 may be utilized to retrieve information corresponding to a tote 50, a product, and/or a storage bin 72. FIGS. 25 through 27 provide flowcharts 780, 800, 820 that illustrates sequences of operations that may be performed by hand scanner 142 consistent with embodiments of the invention to retrieve information stored at pharmacy host server 56 responsive to scanning tote 50, product 36, 38, and/or storage bin 72 with the hand scanner 142. Referring to FIG. 25 and flowchart 780, the operator may scan product barcode 152 with the hand scanner 142 (block 782), and a controller 370 of the hand scanner 142 may receive product identification data from a barcode scanner 144 in communication with the controller 370 (block 784). The hand scanner 142 communicates the product identification data to the pharmacy host server 56, and the pharmacy host server 56 analyzes the received product identification to determine product data fields stored in a product record 386 (block 786). The product data fields may be output on display 146 of the hand scanner 142 by the controller 370 (block 788). The product data fields returned to the operator may include, for example, a medical item included in the product, a dosage, a quantity per unit, a DEA controlled substance classification, assigned storage locations, a quantity on hand, a supplier, a lot number, an expiry date and/or other such information.

Similarly, as shown in FIG. 26 and flowchart 800, the operator may scan a machine readable indicia 116 associated with the storage bin 72 (block 802), and the controller 370 receives a bin identifier based on the scanned indicia from barcode scanner 144 of the hand scanner 142 (block 804). The processor 342 of the pharmacy host server 56 receives the bin identifier and determines bin data fields from a bin record 328 based on the bin identifier (block 806). The bin data fields may be output on the display 146 of the hand scanner 142 for the operator (block 808). Bin data fields returned to the operator may include: a bin size associated with the storage bin 72, a product stocked in the storage bin 72, a lot number of the product, a unit quantity, a DEA controlled substances class number for the product, and/or other such information.

FIG. 27 is a flowchart 820 illustrating a sequence of operations that may occur in response to the operator scanning a machine readable indicia associated with tote 50 with the hand scanner 142 (block 822). The controller 370 receives a tote identifier based on the scanned indicia from barcode scanner 144 of the hand scanner 142 (block 824). The processor 342 of the pharmacy host server 56 receives the bin identifier and determines tote data fields from a tote record 360 based on the tote identifier (block 826). The tote data fields may be output on the display 146 of the hand scanner 142 for the operator (block 828). Bin data fields returned to the operator may include, for example, an associated customer order, associated batch data, labeled and verified products that should be in the tote, a type associated with the tote, and/or other such information. Each of these query functions can be performed without requiring a pharmacist log-in because these queries do not require movement of products in the ALV system 30.

The ALV process may also include several restocking and replenishment tasks and different levels of priorities for replenishment based on conditions. For instance, the ALV and (optionally) the ULV, CLV, and LVK systems in conjunction with the pharmacy host system 56 will keep a complete in-pharmacy inventory count for all medical items used within. This will include a warehouse stock location, a back stock location, and a forward stock location (e.g., at the storage carousels 62). Items received at the receiving dock will be transacted as part of the receiving process into one of these three locations, based on the quantity on hand for each of the three locations. When the quantity on hand at the forward stock location (e.g. storage carousels in the ALV, ULV or a shelf location outside of the LVK) is below par level, a replenishment task is generated for the ALV/ULV. If the number of outstanding orders for that medication item is less than the remaining quantity on hand, then the request is considered to be a low level replenishment task. If the number of outstanding orders for that medication item is greater than the remaining quantity on hand, then the request is considered to be a high level replenishment task. Via the handheld manual scanners, the operator will be prompted to replenish the forward stock location from a specific back stock location (if there is one) or directly from the warehouse stock location when a back stock location does not exist or was assigned or if the quantity on hand for a specific back stock location is zero. Otherwise, it is a FEFO then FIFO pull of inventory through the pharmacy to each one of these stocking locations. The inventory across each of the filling systems in the pharmacy can be monitored and controlled for various reasons. Because items are not depleted from inventory until a patient label is confirmed on the product (or when the product is placed in a reject bin for restocking, which takes the product out of "on-hand" inventory only), the rates of how particular items are being requested from stock can be determined and analyzed to determine if the size of storage locations for those particular items needs to be adjusted to make more room or less room for these particular items. In this regard, the storage capacity of the storage locations is continuously optimized based on the output of the pharmacy.

Although the storage carousel 62 shown with the ALV system 30 has been described with a control process to deliver batches of medical items or products to an operator for labeling and verification at the ALV machine 44, the storage carousel 62 may also be used in connection with other types of product form factors with a manual-scan kiosk located adjacent to the storage carousel 62 in other embodiments. For example, such a universal label and verification system has been concurrently developed as described in U.S. patent application Ser. No. 13/801,017 to Carson et al., entitled "Universal Label and Verification Systems and Methods for Filling Customer Orders of Medical Items", which is co-owned by the assignee of the present invention and is hereby incorporated by reference herein in its entirety.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "includes", "having", "has", "with", "comprised of", or variants thereof are used in either the detailed description or the claims, such terms are intended to be inclusive in a manner similar to the term "comprising."

While the invention has been illustrated by a description of various embodiments and while these embodiments have been described in considerable detail, it is not the intention of the applicants to restrict or in any way limit the scope of the appended claims to such detail. In particular, any of the blocks of the above flowcharts may be deleted, augmented, made to be simultaneous with another, combined, or be otherwise altered in accordance with the principles of the invention. Additional advantages and modifications will readily appear to those skilled in the art. The invention in its broader aspects is therefore not limited to the specific details, representative methods, and illustrative examples shown and described. Accordingly, departures may be made from such details without departing from the spirit or scope of applicants' general inventive concept.

What is claimed is:

1. A method for filling a customer order containing at least one product to be labeled and verified before delivery to a predetermined customer associated with the customer order, each product including a medical item, and the method comprising:
   receiving a batch of products to be picked from a storage carousel surrounded by a cage having a door, the batch of products including medical items contained in the customer order;
   generating pick instructions including an indication of a storage location in the storage carousel for each of the batch of products to be picked;

determining a sequence of products to be removed from the storage carousel by determining the most efficient manner of presenting the products to the door of the cage, including identifying any groups of products in one or more storage locations that may be presented to the door of the cage simultaneously;

rotating the storage carousel to move a first storage location holding a first product of the batch of products adjacent to the door of the cage to provide access for a user to remove the first product from the first storage location;

prompting a user to remove the first product by illuminating an associated pick module on the cage located adjacent to the first storage location;

receiving input from the user that confirms removal of the first product from the storage carousel;

minimizing movements of the storage carousel during retrieval of the batch by following the sequence of products during completion of the rotating, prompting, and receiving input steps;

repeating the rotating, prompting, and receiving input steps until all of the products for the batch of products have been removed from the storage carousel; and labeling the products with a patient label and verifying that a correct patient label was applied to each of the products in the customer order, thereby making the customer order ready for delivery to the predetermined customer.

2. The method of claim 1, wherein the products each include a product label, and labeling the products with a patient label and verifying that a correct patient label was applied further comprises:

prompting the user to insert the batch of products into product inlets associated with an automated label and verification machine;

labeling each of the batch of products with a patient label with the automated label and verification machine; and verifying that the product label and the patient label are correctly applied to each of the products inserted into the automated label and verification machine.

3. The method of claim 2, wherein the labeling and verifying steps of the automated label and verification machine further comprise:

automatically verifying the product label on each of the products with the automated label and verification machine;

transferring each of the products with a verified product label onto a conveyor that defines a workflow path for processing the products;

printing a patient label for each of the products moving along the workflow path;

applying the patient labels to the products moving along the workflow path; and after the patient label is applied to each of the products, independently verifying that the product label matches the patient label on each of the products moving along the workflow path.

4. The method of claim 1, wherein receiving the batch of products to be picked further comprises:

receiving a batch of products located in a plurality of storage carousels, with each storage carousel surrounded by a cage having a door; and wherein the method further comprises:

prompting a user to move to a different one of the plurality of storage carousels after each of the products contained in a first storage carousel have been removed from the first storage carousel.

5. The method of claim 4, wherein the batch of products also includes products located in pick-to-light racks, and the method further comprises:

prompting a user to move to one of the pick-to-light racks holding at least one of the batch of products; and illuminating storage locations on the pick-to-light rack holding the products to be removed by the user to provide pick instructions to the user.

6. The method of claim 1, wherein receiving input from the user that confirms removal of the first product further comprises:

receiving input from a press button located on the associated pick module located adjacent to the first storage location when the user confirms removing the first product by depressing the press button.

7. The method of claim 1, wherein receiving input from the user that confirms removal of the first product further comprises:

receiving input transmitted from a hand scanner carried by the user when the user confirms removing the first product by scanning the first product, the hand scanner also including a human machine interface (HMI) for providing prompts to the user.

8. The method of claim 1, wherein the storage carousel also includes a light curtain optical sensor located adjacent to the door, and rotating the storage carousel to move a first storage location further comprises:

detecting with the light curtain optical sensor an entry of a user's arm into the storage carousel from outside the cage; and stopping rotating movement of the storage carousel whenever the user's arm is detected by the optical sensor to avoid injuring the user.

9. A method for filling a customer order containing at least one product to be labeled and verified, each product including a medical item, the products being picked from a storage carousel surrounded by a cage having a door and including storage bins holding controlled substances, the door on a cage being motorized, the storage bins in the storage carousel defining separated vertical columns containing groups of storage bins that may be presented simultaneously for access at the door of the cage, and, when a first product is a controlled substance, the method comprising:

maintaining controlled substances of different schedule levels in different vertical columns of the storage carousel, thereby separating controlled substances of different schedule levels in independent pie-piece-shaped portions of the storage carousel;

receiving a batch of products to be picked from the storage carousel, the batch of products including medical items contained in the customer order;

closing the motorized door to prevent access to the storage bins of the storage carousel before providing any pick instructions to the user to remove a product from the storage carousel;

verifying identification data provided by the user to determine if the user is authorized to remove controlled substances from the storage carousel;

generating pick instructions including an indication of a storage location in the storage carousel for each of the batch of products to be picked;

rotating the storage carousel to move a first storage location holding the first product of the batch of products adjacent to the door of the cage to provide access for a user to remove the first product from the first storage location such that the portions of the storage carousel containing controlled substances of a schedule level higher than what the user is authorized to remove are never rotated past the door, thereby preventing a user from having even temporary access to controlled substances of a schedule level higher than what the user is authorized to remove;

opening the motorized door to provide access to the storage carousel only when the identification data has been verified and only after the first storage location has been rotated to the door of the cage;

prompting a user to remove the first product by illuminating an associated pick module on the cage located adjacent to the first storage location;

receiving input from the user that confirms removal of the first product from the storage carousel;

repeating the rotating, prompting, and receiving input steps until all of the products for the batch of products have been removed from the storage carousel; and labeling the products with a patient label and verifying that a correct patient label was applied to each of the products in the customer order.

10. The method of claim 1, wherein a particular product stored in the storage carousel is located in a plurality of storage locations, and generating pick instructions including an indication of a storage location in the storage carousel for each of the batch of products to be picked further comprises:

selecting which of the plurality of storage locations for the particular product should be presented to the door of the cage using at least one of: "First In First Out" logic to remove products placed in the storage carousel earliest, or "First Expired First Out" logic to remove products that will expire soonest from the storage carousel.

11. The method of claim 1, wherein when the storage carousel is to be refilled with products between filling of customer orders, the method further comprises:

prompting a user to input data specifying a product to be restocked and a quantity of the product available to place into the storage carousel;

determining at least one storage location free to receive the product based on the input data specifying the product to be restocked;

rotating the storage carousel to present the at least one storage location to the door of the cage;

selectively operating the pick modules associated with the at least one storage location to prompt the user to place the product to be restocked into the at least one storage location;

receiving an indication from the user that the product has been restocked into the at least one storage location; and repeating the prompting, determining, rotating, selectively operating, and receiving an indication steps for each other product to be restocked.

12. A system configured to fill a customer order containing at least one product to be labeled and verified before delivery to a predetermined customer associated with the customer order, each product including a medical item, and the system comprising:

a storage carousel including a plurality of storage bins on a plurality of shelves, each storage bin configured to receive bulk inventory of a product;

a cage surrounding the storage carousel, the cage including a door configured to provide selective access to one of the storage bins on each shelf of the storage carousel;

a plurality of pick modules mounted on the cage adjacent to the door, each pick module being associated with one of the shelves of the storage carousel;

a controller having a processor and a memory;

program code resident in the memory and configured to be executed by the processor to identify a customer order and receive a batch of products to be picked from the storage carousel, the batch of products including medical items contained in the customer order, determine a sequence of products to be removed from the storage carousel by determining the most efficient manner of presenting the products to the door of the cage, including identifying any groups of products in one or more storage locations that may be presented to the door of the cage simultaneously, actuate rotation of the storage carousel to provide access to one of the products in the batch and to minimize movements of the storage carousel during retrieval of the batch by following the sequence of products, prompt the user to remove the product from the storage carousel by illuminating the pick modules, and continue rotation and illumination steps until all products for the batch have been removed from the storage carousel; and an automated label and verification machine configured to receive the batch of products, label the products with patient labels, and verify that the patient labels match product labels located on the products, thereby making the customer order ready for delivery to the predetermined customer.

13. The system of claim 12, wherein the automated label and verification machine further comprises:

a conveyor defining a workflow path for processing the products;

a label application station arranged about the workflow path and configured to print and apply a patient label onto each of the products;

a vision inspection station arranged about the workflow path, the vision inspection station configured to independently verify that the product label on each of the products matches a patient label after application of the patient label to the product; and an unloading station configured to transfer labeled and verified products away from the conveyor.

14. The system of claim 12, further comprising:

a plurality of storage carousels each including a plurality of storage bins on a plurality of shelves, a cage, a door, and pick modules; and a human machine interface configured to provide instructions to the user to indicate which of the plurality of storage carousels to move to in order to pick a product for the customer order.

15. The system of claim 14, wherein the human machine interface includes an alphanumeric display mounted on the cage of each of the storage carousels adjacent to the pick modules.

16. The system of claim 14, wherein the human machine interface includes a display screen on a hand scanner carried by the user between the plurality of storage carousels.

17. The system of claim 12, further comprising:

a light curtain optical sensor coupled to the controller and located adjacent to the door, the optical sensor operable to detect entry of a user's arm into the storage carousel from outside the cage such that the rotation of the storage carousel can be stopped whenever the user's arm is detected by the optical sensor.

18. The system of claim 12, further comprising:

a pharmacy host server communicating with the controller, the server configured to generate batches of products for a customer order and send the batches of products to the controller for use in filling the customer order.

19. The system of claim 12, wherein the door on the cage is motorized, the storage carousel includes storage bins holding controlled substances, the storage bins defining separated vertical columns containing groups of storage bins that may be presented simultaneously for access at the door of the cage, and controlled substances of different schedule levels are maintained in different vertical columns of the storage carousel, thereby separating controlled substances of different schedule levels in independent pie-piece-shaped portions of the storage carousel, and wherein, when the first product is a controlled substance, the program code is configured to be executed by the processor to close the motorized door to prevent access to the storage bins of the storage carousel before providing any pick instructions to the user, verify identification data provided by the user to determine if the user is authorized to remove controlled substances from the storage carousel, rotate the storage carousel such that the portions of the storage carousel containing controlled substances of a schedule level higher than what the user is authorized to remove are never rotated past the door, and open the motorized door to provide access to the storage carousel only when the identification data has been verified and only after the first storage location has been rotated to the door of the cage.

* * * * *